United States Patent
Wu et al.

(10) Patent No.: US 11,130,990 B2
(45) Date of Patent: Sep. 28, 2021

(54) OLIGONUCLEOTIDE PAINTS

(71) Applicant: President and Fellows of Harvard College, Cambridge, MA (US)

(72) Inventors: Chao-ting Wu, Brookline, MA (US); George M. Church, Brookline, MA (US); Benjamin Richard Williams, Seattle, WA (US)

(73) Assignee: President and Fellows of Harvard College, Cambridge, MA (US)

( * ) Notice: Subject to any disclaimer, the term of this patent is extended or adjusted under 35 U.S.C. 154(b) by 505 days.

(21) Appl. No.: 15/726,870

(22) Filed: Oct. 6, 2017

(65) Prior Publication Data

US 2018/0223347 A1    Aug. 9, 2018

Related U.S. Application Data

(63) Continuation of application No. 12/780,446, filed on May 14, 2010, now abandoned.

(60) Provisional application No. 61/288,931, filed on Dec. 22, 2009, provisional application No. 61/183,247, filed on Jun. 2, 2009.

(51) Int. Cl.
*C12Q 1/6841* (2018.01)
*C12Q 1/686* (2018.01)

(52) U.S. Cl.
CPC ........... *C12Q 1/6841* (2013.01); *C12Q 1/686* (2013.01)

(58) Field of Classification Search
CPC .............................. C12Q 1/6841; C12Q 1/686
See application file for complete search history.

(56) References Cited

U.S. PATENT DOCUMENTS

| | | |
|---|---|---|
| 5,447,841 A | 9/1995 | Gray et al. |
| 6,066,459 A | 5/2000 | Garini et al. |
| 2007/0238105 A1 | 10/2007 | Barrett et al. |
| 2009/0082225 A1 | 3/2009 | Gerdes et al. |
| 2010/0055681 A1 | 3/2010 | Yamada |

OTHER PUBLICATIONS

Ashe, et al., "Intergenci transcription and transinduction of the human 13-globin locus," Genes and Development pp. 1-30, Aug. 13, 1997.
Bacher, et al., "Transient Colocalization of X-Inactivation Centres Accompanies the Initiation of X Inactivation," Nature Cell Biology vol. 8, No. 3, Mar. 2006.
Bayani, et al., "Overview of Cytogenetic Chromosome Analysis," Current Protocols in Cell Biology (2004) 22.1.1-22.1.3.
Borst, P., "Antigenic Variation and Allelic Exclusion", Cell vol. 109, Issue 1, Apr. 5, 2002, pp. 5-8.
Boyle, et al. "Fluorescence in situ hybridization with high-complexity repeat-free oligonucleotide probes generated by massively parallel synthesis" Chromosome Res (2011) 19:901-909 Springer.
Chuang, et al., "Regulation of Nuclear Transport and Degradation of the Xenopus Cyclin-dependent Kinase Inhibitor, p27Xic1", www.jbc.org, pp. 1-10, Oct. 23, 2000, DOI 10.1074ljbc.M008896200.

(Continued)

*Primary Examiner* — Jeremy C Flinders
(74) *Attorney, Agent, or Firm* — Banner & Witcoff, Ltd.

(57) ABSTRACT

Novel methods for making high resolution oligonucleotide paints are provided. Novel, high resolution oligonucleotide paints are also provided.

46 Claims, 7 Drawing Sheets

(7 of 7 Drawing Sheet(s) Filed in Color)

(56) References Cited

OTHER PUBLICATIONS

Cooper, et al., "Mutational and selective effects on copy-number variants in the human genome", vol. 39, Jul. 2007 Nature Genetics Supplement.
Cremer et al., Nature Rev. Gen., 2001, 2:292-301.
Danilova, et al., "Integrated Cytogenetic Map of Mitotic Metaphase Chromosome 9 of Maize: Resolution, Sensitivity, and Banding Paint Development," Chromosoma (2008) 117:345-356.
Dejardin, et al., "Purification of Proteins Associated with Specific Genomic Loci", Cell vol. 136, Issue 1, Jan. 9, 2009, pp. 175-186.
Duncan, I., "Transvection Effects in *Drosophila*," Annu. Rev. Genet. 2002, 36:521-56.
Edwards, et al., "Mechanisms regulating imprinted genes in clusters", Current Opinion in Cell Biology 2007, 19:281-289.
Fransz, et al., "Interphase chromosomes in *Arabidopsis* are organize as well defined chromocenters from which euchromatin loops emanate", 14584-14589, PNAS, Oct. 29, 2002, vol. 99, No. 22.
Gall, Joseph G, et al., "Nucleic Acid Hybridization in Cytological Preparations," Methods in Enzymology, vol. 21, 1971, pp. 470-480.
Grant-Downton, et al., "Plants, Pairing and Phenotypes—Two's Company?" Trends in Genetics vol. 20, No. Apr. 4, 2004.
Hartl, et al., "Chromosome Alignment and Transvection Are Antagonized by Condensin II", Science vol. 322, No. 5906, pp. 1384-1387, Nov. 2008.
Henderson, et al., Excerpt from "International Review of Cytology," vol. 76, pp. 1-46 (1982).
Koeman, et al., "Somatic Pairing of Chromosome 19 in Renal Oncocytoma Is Associated with Deregulated ELGN2-Mediated Oxygen-Sensing Response", PLoS Genet Sep. 2008, vol. 4, No. 9.
Ling, et al., CTCF Mediates Interchromosomal Colocalization Between Igf2/H19 and Wsb1/Nf, Science vol. 312, Apr. 14, 2006.
Matsuda, et al., "Cryptic Insertion into 11q23 of MLL T10 Not Involved in t(1 ;15;11;10)(p36;q11 ;q23;q24) in Infant Acute Biphenotypic Leukemia," Cancer Genetics and Cytogenetics 190 (2009) 113-120.
Matzke, et al., "Planting the Seeds if a New Paradigm," PLOS Biology, vol. 2, No. 5, May 2004.
McKee, B., "Homologous Pairing and Chromosome Dynamics in Meiosis and Mitosis," Biochimica et Biophysica Acta 1677 (2004) 165-180.
Morris, et al., "Two modes of tranvection: Enhancer action in trans and bypass of a chromatin insulator in cis", Proc. Natl. Acad. Sci USA vol. 95, p. 10740-10745, Sep. 1998 Genetics.
Ohlsson, et al., "The 4C technique: the 'Rosetta stone' for genome biology in 3D?", Current Opinion in Cell Biology 2007, 19:321-325.
Osborne, et al., "Myc Dynamically and Preferentially Relocates to a Transcription Factory Occupied by Igh", 2007 PLoS Biology 5(8); e192. doi:10 1371~ournal.pbio.0059192.
Pauler, et al., "Silencing by imprinted noncoding RNAs: is transcription the answer?", Trends in Genetics vol. 23, No. 6, 2007.
Ried, et al., "simultaneous visualization of seven different DNA probes by in situ hybridization using combinatorial fluorescence and digital imaging microscopy", Proc. Natl. Acad. Sci. USA, vol. 89, pp. 1388-1392, Feb. 1992, Genetics.
Roberts, et al., "Novel Method for the Production of Multiple Colour Chromosome Paints for Use in Karyotyping by Fluorescence In Situ Hybridisation," Genes, Chromosomes & Cancer 25:241-250 (1999).
Schrock, et al., "Multicolor Spectral Karyotyping of Human Chromosomes", Science vol. 273, Jul. 26, 1996.
Selker, E., "Genome Defense and DNA Methylation in Neurospora," Cold Spring Harb Symp Quant Biol 2004 69:119-124.
Singh and Kumar (Molecular Biology Today (2001) 2(2): 27-32).
Speicher, M., "Karyotyping Human Chromosomes by Combinatorial Multi-Fluor FISH," Nature Genetics, vol. 12, Apr. 1996.
Turner, James M., "Meiotic sex chromosome inactivation", Development 134, 1823-1831, May 15, 2007.
Walder et al.. Nucleic Acids Research, 1993, 21 (8):4339-4343.
Williams, et al., "Disruption of Topoisomerase II Perturbs Pairing in *Drosophila* Cell Culture", Genertics, vol. 177,31-46, Sep. 2007.
Wu, et al., "Transvection and Other Homology Effects," Current Opinion in Genetics and Development 1999, 9:237-246.
Xu, et al., "Transient Homologous Chromosome Pairing Marks the Onset of X Inactivation", Science, vol. 311, Feb. 24, 2006.
Yamada, et al., "Visualization of Fine-Scale Genomic Structure by Oligonucleotide-Based High-Resolution FISH," Cytogenet Genome Res 2011;132:248-254, Karger.
Yang, et al., "Noncoding RNAs and Intranuclear Positioning in Monoallelic Gene Expression", Cell 128, 777-786, Feb. 23, 2007.
Zickler, D., "From Early Homologue Recognition to Synaptonemal Complex Formation," Chromosoma (2006) 115:158-174.
Player et al. "Single-copy Gene Detection Using Branched DNA (bDNA) In Situ Hybridization" The Journal of Histochemistry & Cytochemistry, vol. 49(5), pp. 603-611m 2001.

OLIGONUCLEOTIDE PAINTS

RELATED APPLICATIONS

This application is a continuation application which claims priority to U.S. patent application Ser. No. 12/780,446, filed on May 14, 2010, which claims the benefit of U.S. provisional patent application Nos. 61/183,247, filed Jun. 2, 2009, and 61/228,931, filed Dec. 22, 2009, each of which are hereby incorporated by reference in their entireties.

STATEMENT OF GOVERNMENT INTERESTS

This invention was made with Government support under the National Institutes of Health grant number GM085169-01A1. The Government has certain rights in the invention.

FIELD

Embodiments of the present invention relate in general methods for making and using oligonucleotide paints for chromosome analysis methods.

BACKGROUND

Cytogeneticists have been working hand-in-hand with geneticists and molecular geneticists to clarify the processes of inheritance and gene expression ever since the synergy of August Weissman's chromosome theory of inheritance, as interpreted by Boveri and Sutton in 1902, with Mendel's theory of inheritance, as brought forth by Morgan, Sturtevant, Muller, and Bridges in their landmark 1915 publication, *The Mechanism of Mendelian Heredity*. This synergy, however, has become technologically unbalanced, as the tools for dissecting gene expression outstrip those with which cytogeneticists tease apart the arrangement of chromosomes within the nucleus or their behavior as they or are inherited from cell-to-cell or generation-to-generation.

Chromosome arrangement and behavior cannot be extracted, purified or captured. Chromosomes have no unit structure that can be isolated and crystallized, and they produce no product or enzymatic activity that can be assayed in a test tube. Instead, researchers must study chromosome arrangement and behavior in situ, visualizing them with cytological tools or via genetic manipulation. Constrained as well as guided by these requirements, remarkable technologies have nonetheless been developed. Cytology-grade microscopes, electron microscopes, chromosome stains, and in situ hybridization protocols have all greatly advanced the ability of scientists to study how chromosome organization impacts gene expression and development. For example, the use of fluorescent in situ hybridization (FISH) to reveal the colocalization of the Myc and Igh genes in transcription factories, provides a plausible explanation for the frequency with which these two genes, lying on different chromosomes, become fused through translocations associated with plasmacytoma and Burkitt lymphoma (Osborne et al. (2007) *PLoS Biol.* 5(8):e192). Studies such as this can only be carried out in situ, highlighting the need for cytological technologies. Most recently, the technology of chromosome conformation capture (Ohlsson et al. (2007) *Curr. Opin. Cell Biol.* 19(3):321) has fused molecular biological tools and cytological tools to capture and clone chromosomal regions that come into contact, generating tremendous excitement among geneticists and cytogeneticists. Although indirect, genetic approaches have elucidated the manner by which chromosomes are transmitted through mitosis and meiosis into subsequent cellular and organismal generations and, through the use of translocations and chromosomal rearrangements, demonstrated how chromosome positioning and interchromosomal interactions can profoundly affect gene expression (Wu et al. (1999) *Curr. Opin. Gen. Dev.* 9:237; Duncan (2002) *Ann. Rev. Genet.* 36:521; Grant-Downton, et al. (2004) *Trends Genet.* 20:188; McKee (2004) *Biochim Biophys Acta* 1677:165; Zickler (2006) *Chromosoma* 115:158).

Still, scientists remain tremendously limited in the ability to understand the relationship between chromosome arrangement and gene expression. Foremost among these needs are technologies that will permit the visualization of chromosome arrangement, single nucleus by single nucleus, a need that grows as evidence accumulates steadily for the roles that chromosome positioning and interchromosomal interactions play in the regulation of genes and development in humans and other mammals, *Drosophila*, plants, nematodes, fungi and, essentially, every species.

SUMMARY

Chromosome paints are detectable markers that label chromosomes along their entire length, permitting physicians and researchers to identify chromosomes and decipher chromosome rearrangements. However, commercially available paints are expensive for routine and frequent use, ranging between $100 to $4,000 or more per whole genome, per assay, with increased resolution requiring more expensive paints. As such, many researchers have not utilized chromosome paints for systematic genome-wide analysis and have, instead, used the existing chromosome paint technology sparingly.

It has been surprisingly discovered that chromosome paints having superior resolution and labeling functionality can be economically generated using the methods described herein. It has been discovered that the per assay cost of chromosome paints could be reduced approximately 50- to 4,000-fold while increasing resolution by 100- to 1,000-fold or more, thus rendering possible many diagnoses and research projects that would otherwise not be performed or considered due to prohibitive cost. For example, the methods and compositions described herein can be used to produce paints for all chromosomes of the human genome for as little as $1 to $2 per assay.

Accordingly, a first method of making a set of high resolution oligonucleotide paints is provided. The method includes the steps of providing at least one solid support having a plurality of synthetic, single stranded oligonucleotide sequences attached thereto, wherein a portion of each of the plurality of synthetic, single stranded oligonucleotide sequences is complementary to a portion of a specific chromosome sequence, synthesizing a plurality of complementary strands, each of which is complementary to a synthetic, single stranded oligonucleotide sequence attached to the at least one solid support, removing the plurality of complementary strands from the at least one solid support, amplifying the plurality of complementary strands, and labelling the plurality of complementary strands to produce a set of oligonucleotide paints, wherein the set oligonucleotide paints has a resolution of about two kilobases or fewer. In certain aspects, each oligonucleotide paint has a resolution of about one kilobase or fewer or 100 bases or fewer. In certain aspects, the set of oligonucleotide paints has a resolution of between about 20 bases and about 30 bases. In certain aspects, the length of each of the oligonucleotide sequences is about 60 bases (e.g., about 14 bases at each of the 3' and 5' ends of an oligonucleotide sequence are primer sequences and about 32 bases internal to the primer sequences are complementary to a chromosome sequence). In other aspects, each of the oligonucleotide paints has a detectable and/or retrievable label attached thereto. In certain aspects, the retrievable label further binds a moiety selected from the group consisting of a protein, a peptide, a DNA sequence, an RNA sequence and a carbohydrate. In other aspects, the retrievable moiety is exposed to light, heat or a chemical to activate binding of the retrievable label to a moiety selected from the group consisting of a protein, a peptide, a DNA sequence, an RNA sequence and a carbohydrate. In certain aspects, each of the oligonucleotide paints has a detectable label attached thereto. In certain aspects, the detectable label is a fluorescent label. In other aspects, the set of oligonucleotide paints provides one spectrally resolvable color, or at least 2, 3, 4, 5, 6, 7, 8, 9, 10, 11, 12, 13, 14, 15, 16, 17, 18, 19, 20, 21, 22, 23, 24, 25, 50, 100, 200, 300, 400, 500 or more spectrally resolvable labels and/or the set of oligonucleotide paints provides a spectrally resolvable label for each chromosome and/or one or more sub-chromosomal regions of an organism. In certain aspects, the plurality of synthetic, single stranded oligonucleotide sequences encodes 1%, 2%, 3%, 4%, 5%, 10%, 15%, 20%, 25%, 30%, 35%, 40%, 45%, 50%, 55%, 60%, 66%, 70%, 75%, 80%, 85%, 90%, 95%, 99% or more (e.g., 100%) of a genome (e.g., a human genome) or between 1% and 75%, between 5% and 50%, between 5% and 25%, between 5% and 75%, between 10% and 50% or between 20% and 40% of a genome (e.g., a human genome). In certain aspects, at least 25 microarrays or at least 100 microarrays are provided that are optionally generated and/or utilized in parallel. In still other aspects, the step of amplifying includes providing a plurality of primers (e.g., universal primers), each of which is complementary to a portion of a complementary strand or a portion of a single stranded oligonucleotide sequence. In yet other aspects, at least a portion of each of the primer sequences is removable after the amplification step. In certain aspects, the universal primers comprise between one and 1000 different sequences or comprise at least 1000 different sequences. In other aspects, a set of oligonucleotide paints produced by the first method is provided. In still other aspects, a method of detecting a chromosome rearrangement in a biological sample (e.g., one or more of translocation, insertion, inversion, deletion, duplication, transposition, aneuploidy, polyploidy, complex rearrangement and telomere loss) including the steps of providing a biological sample, contacting the biological sample with the set of oligonucleotide paints of the first method, detecting binding of the set of oligonucleotide paints, comparing the binding of the set of oligonucleotide paints to a standard, and detecting a chromosome rearrangement if binding of the set of oligonucleotide paints differs from the standard is provided.

A second method of making a set of oligonucleotide paints is provided. The method includes the steps of providing at least one solid support having a plurality of synthetic, single stranded oligonucleotide sequences attached thereto, wherein a portion of each of the plurality of synthetic, single stranded oligonucleotide sequences is complementary to a portion of a specific chromosome sequence and wherein each specific chromosome sequence excludes highly repetitive elements (and/or any other genomic sequence that one wants to exclude), synthesizing a plurality of complementary strands, each of which is complementary to a synthetic, single stranded oligonucleotide sequence attached to the at least one solid support, removing the plurality of complementary strands from the at least one solid support, amplifying the plurality of complementary strands, and labelling the plurality of complementary strands to produce a set of oligonucleotide paints. In certain aspects, each specific chromosome sequence excludes repetitive elements present in the genome as two copies, three copies or four copies (i.e., in a haploid genome). In other aspects, the length of each of the oligonucleotide sequences is about 60 bases (e.g., about 14 bases at each of the 3' and 5' ends of an oligonucleotide sequence are primer sequences and about 32 bases internal to the primer sequences are complementary to a chromosome sequence). In certain aspects, each of the oligonucleotide paints has a retrievable label attached thereto. In certain aspects, the retrievable label further binds a moiety selected from the group consisting of a protein, a peptide, a DNA sequence, an RNA sequence and a carbohydrate. In other aspects, the retrievable moiety is exposed to light, heat or a chemical to activate binding of the retrievable label to a moiety selected from the group consisting of a protein, a peptide, a DNA sequence, an RNA sequence and a carbohydrate. In certain aspects, each of the oligonucleotide paints has a detectable label attached thereto. In certain aspects, the detectable label is a fluorescent label. In other aspects, the set of oligonucleotide paints provides one spectrally resolvable color, or at least 2, 3, 4, 5, 6, 7, 8, 9, 10, 11, 12, 13, 14, 15, 16, 17, 18, 19, 20, 21, 22, 23, 24, 25, 50, 100, 200, 300, 400, 500 or more spectrally resolvable labels and/or the set of oligonucleotide paints provides a spectrally resolvable label for each chromosome and/or one or more sub-chromosomal regions of an organism. In certain aspects, the plurality of synthetic, single stranded oligonucleotide sequences encodes 1%, 2%, 3%, 4%, 5%, 10%, 15%, 20%, 25%, 30%, 35%, 40%, 45%, 50%, 55%, 60%, 66%, 70%, 75% or more of a genome (e.g., a human genome) or between 1% and 75%, between 5% and 50%, between 5% and 25%, between 5% and 75%, between 10% and 50% or between 20% and 40% of a genome (e.g., a human genome). In certain aspects, at least 25 microarrays or at least 100 microarrays are provided that are optionally generated and/or utilized in parallel. In still other aspects, the step of amplifying includes providing a plurality of primers (e.g., universal primers), each of which is complementary to a portion of a complementary strand or a portion of a single stranded oligonucleotide sequence. In yet other aspects, at least a portion of each of the primer sequences is removable after the amplification step. In certain aspects, the universal primers comprise between one and 1000 different sequences or comprise at least 1000 different sequences. In other aspects, a set of oligonucleotide paints produced by the second method is provided. In still other aspects, a method of detecting a chromosome rearrangement in a biological sample (e.g., one or more of translocation, insertion, inversion, deletion, duplication, transposition, aneuploidy, polyploidy, complex rearrangement and telomere loss) including the steps of providing a biological sample, contacting the biological sample with the set of oligonucleotide paints of the second method, detecting binding of the set of oligonucleotide paints, comparing the binding of the set of oligonucleotide paints to a standard, and detecting a chromosome rearrangement if binding of the set of oligonucleotide paints differs from the standard is provided.

In certain exemplary embodiments, a palette of oligonucleotide paints including a plurality of oligonucleotide sequences, wherein each oligonucleotide sequence is complementary to a single type of mutation corresponding to one of a specific set of chromosome abnormalities associated with a disorder, and wherein the set comprises at least 50 different types of mutations is provided. In certain aspects, the set includes at least 100 different types of mutations, at least 1000 different types of mutations, at least 10,000 different types of mutations or more.

In certain exemplary embodiments a kit (e.g., a diagnostic kit) including the set of oligonucleotide paints of the first or second method is provided. In certain aspects the kit includes instructions for use. In other aspects, the kit is used to determine the karyotype of a sample.

In certain exemplary embodiments, an article of manufacture for making a set of high resolution oligonucleotide paints is provided, including a plurality of microarrays, each microarray having a plurality of synthetic oligonucleotide sequences attached thereto, wherein a portion of each of the plurality of synthetic oligonucleotide sequences is complementary to a portion of a specific chromosome sequence, wherein the sum of synthetic oligonucleotide that are complementary corresponds to between about 5% and 25% of a genome of interest, and wherein the set of oligonucleotide paints has a resolution of about two kilobases or fewer. In other aspects, the plurality of synthetic oligonucleotide sequences is complementary to approximately 1%, 2%, 3%, 4%, 5%, 10%, 15%, 20%, 25%, 30%, 35%, 40%, 45%, 50%, 55%, 60%, 66%, 70%, 75% or more of a genome (e.g., a human genome). In still other aspects, the article of manufacture further includes a plurality of primers (e.g., universal primers).

In certain exemplary embodiments, a method of preparing a plurality of high resolution oligonucleotide paints comprising computationally determining genomic spacing of a plurality of synthetic, oligonucleotide sequences, wherein each of the plurality is complementary to a portion of a specific chromosome sequence, synthesizing the plurality of synthetic oligonucleotide sequences, and labelling the plurality of synthetic oligonucleotide sequences with a detectable label to produce a plurality of oligonucleotide paints, wherein the set of oligonucleotide paints has a resolution of about two kilobases or fewer, and wherein each of a plurality of the oligonucleotide paints is complementary to a target nucleic acid sequence (e.g., a genomic sequence) of 40 consecutive nucleotide bases or fewer is provided. In certain aspects, the plurality of the oligonucleotide paints is complementary to a target nucleic acid sequence of 30, 20, 10 or fewer consecutive nucleotide bases. In certain aspects, the method further includes the step of computationally selecting at least one detectable label to label each of the plurality of synthetic, oligonucleotide sequences. In other aspects, the method further includes the step of computationally determining the presence of single nucleotide polymorphisms in a genomic sequence of interest to reduce synthesis of synthetic oligonucleotide sequences that bind to repeated regions of the genomic sequence of interest.

In certain exemplary embodiments, a method of making a set of high resolution oligonucleotide paints comprising providing at least one solid support having a plurality of synthetic, single stranded oligonucleotide sequences attached thereto, wherein a portion of each of the plurality of synthetic, single stranded oligonucleotide sequences is complementary to a portion of a specific chromosome sequence, synthesizing a plurality of complementary strands, each of which is complementary to a synthetic, single stranded oligonucleotide sequence attached to the at least one solid support, removing the plurality of complementary strands from the at least one solid support, amplifying the plurality of complementary strands, and labelling the plurality of complementary strands to produce a set of high resolution oligonucleotide paints, wherein each of a plurality of the oligonucleotide paints is complementary to a target nucleic acid sequence of 40 consecutive nucleotide bases or fewer is provided. In certain aspects, the plurality of the oligonucleotide paints is complementary to a target nucleic acid sequence of 30, 20, 10 or fewer consecutive nucleotide bases. In certain aspects, the oligonucleotide paints can cross a cell membrane and/or a nuclear membrane. In other aspects, the oligonucleotide paints include a detectable label (e.g., a fluorescent label) and a quencher. The quencher can optionally be released during the step of extension. In certain aspects, the target nucleic acid sequences are present in a multi-well (e.g., a 384-well) plate. In other aspects, hybridized oligonucleotide paints are detected by fluorescent in situ hybridization (FISH). In certain aspects, the target nucleic acid sequence is genomic.

In other aspects, a method described herein further includes the step of hybridizing the oligonucleotide paints to one or more target sequences. In still other aspects, a method described herein further includes the step of extending the plurality of hybridized oligonucleotide paints (e.g., by primer extension). In yet other aspects, a method described herein includes the step of washing the extended plurality of hybridized oligonucleotide paints under stringent conditions. In other aspects, a method described herein further includes the step of hybridizing the oligonucleotide paints to one or more target sequences in the presence of an enzyme selected from the group consisting of one or more of a proteinase, a lipase, and a ribonuclease.

Further features and advantages of certain embodiments of the present invention will become more fully apparent in the following description of the embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION

Figure 1:
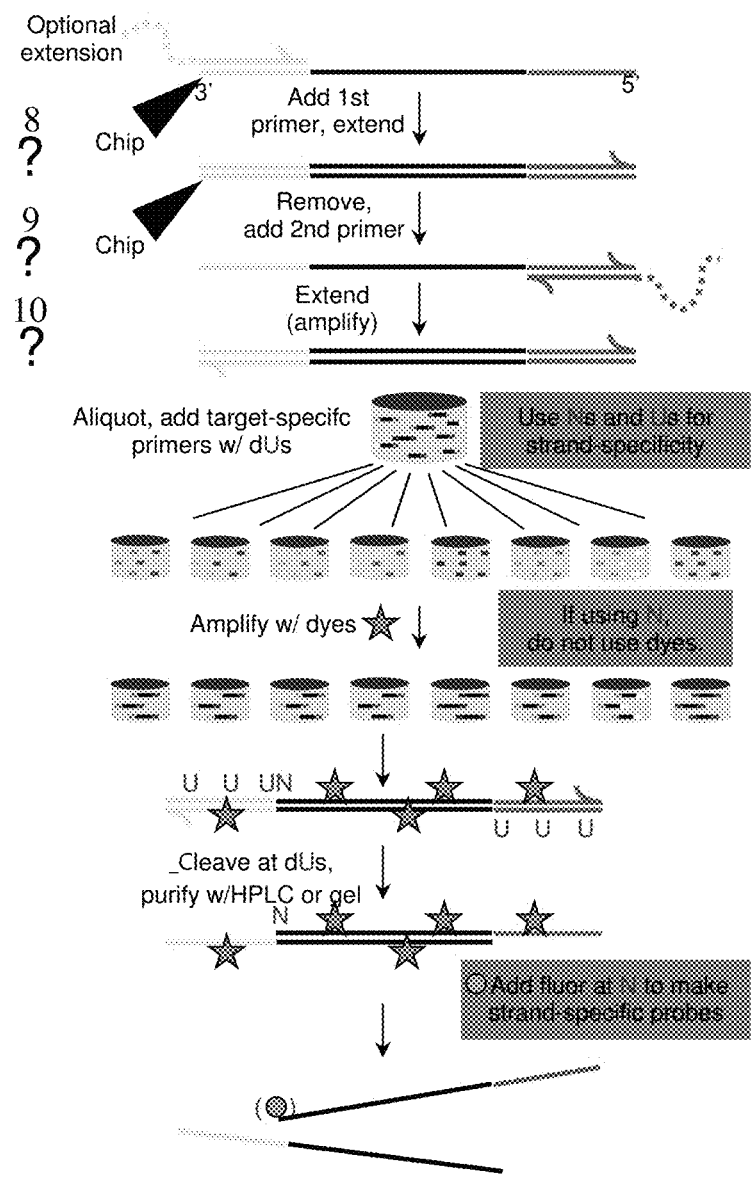
FIG. 1 schematically depicts one method of making of chromosome paints (i.e., Oligopaints) from oligonucleotides.

The principles of the present invention may be applied with particular advantage in methods of tagging (i.e., painting with chromosome paints) one or more oligonucleotide sequences, e.g., chromosome regions (e.g., sub-chromosomal regions) and/or one or more entire chromosomes. The methods described herein create chromosome paints that have an increased resolution over commercially available chromosome paints, which is due in part to the fact that the chromosome paints are synthesized using a specific set of primers, which can amplify and label specific sequences with near absolute certainty. Thus, the chromosome paints described herein have a theoretical resolution on the order of base pairs.

Exemplary embodiments of the present invention are directed to methods for generating novel chromosome paints using synthetic genomic template sequences (e.g., genomic template sequences that have been synthesized on arrays). The synthetic genomic template sequences can be, for example, synthetic genomic template sequences that are generated on and subsequently released from an array into one or more pools, or extension products which are made using synthetic genomic template sequences attached to an array as a template and then released into one or more pools by melting. The released sequences are then amplified and labeled to produce chromosome paints. By designing synthetic genomic template sequences to be flanked by primer sequences, the primers can be used both to label the synthetic genomic template sequences as well as to amplify the genomic sequence. Labeling a chromosome paint can be performed by a variety of methods including, but not limited to, using primers that have been pre-labeled, incorporating labels during amplification or indirect labeling. Labels and methods of incorporating labels into oligonucleotide sequences are discussed further herein.

As used herein, the term "chromosome paint" refers to detectably labeled polynucleotides that have sequences complementary to DNA sequences from a particular chromosome or sub-chromosomal region of a particular chromosome. Chromosome paints that are commercially available are derived from fluorescence activated cell sorted (FACS) and/or flow sorted chromosomes or from bacterial artificial chromosomes (BACs) or yeast artificial chromosomes (YACs). As such, chromosome paints known in the art at the time of filing were laborious to generate and are limited in their resolution.

As used herein, the term "Oligopaint" refers to detectably labeled polynucleotides that have sequences complementary to an oligonucleotide sequence, e.g., a portion of a DNA sequence e.g., a particular chromosome or sub-chromosomal region of a particular chromosome. Oligopaints are generated from synthetic probes and arrays that are, optionally, computationally patterned (rather than using natural DNA sequences and/or chromosomes as a template).

Since Oligopaints are generated using nucleic acid sequences that are present in a pool, they are no longer spatially addressable (i.e., no longer attached to an array). Surprisingly, however, this method increases resolution of the chromosome paints over those that are made using yeast artificial chromosomes (YACs), bacterial artificial chromosomes (BACs), and/or flow sorted chromosomes. In certain aspects, the Oligopaints described herein have a resolution that is, e.g., 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 350%, 400%, 450%, 500%, 600%, 700%, 800%, 900%, 1000%, 2000%, 3000%, 4000%, 5000%, 6000%, 7000%, 8000%, 9000%, 10,000%, 100,000%, 1,000,000%, 10,000,000%, 100,000,000% or greater than chromosome paints that are commercially available.

Typically, chromosome paints that are commercially available have a chromosome resolution on the order of at least $6\times10^6$ base pairs. The Oligopaints described herein, however, have a much higher resolution when compared with paints known in the art. As used herein, the term "resolution" refers to the ability to distinguish (e.g., label) between two points on a polynucleotide sequence (e.g., two points along the length of a chromosome). As used herein, the term "high resolution" refers to the ability to detect two or more nucleic acid sequences having a distance of less than $6\times10^6$ base pairs apart (e.g., on a chromosome). In certain aspects, two or more high resolution Oligopaints have a resolution of about 500 kilobases apart or fewer, 400 kilobases apart or fewer, 300 kilobases apart or fewer, 200 kilobases apart or fewer, 100 kilobases apart or fewer, 90 kilobases apart or fewer, 80 kilobases apart or fewer, 70 kilobases apart or fewer, 60 kilobases apart or fewer, 50 kilobases apart or fewer, 40 kilobases apart or fewer, 30 kilobases apart or fewer, 20 kilobases apart or fewer, 19 kilobases apart or fewer, 18 kilobases apart or fewer, 17 kilobases apart or fewer, 16 kilobases apart or fewer, 15 kilobases apart or fewer, 14 kilobases apart or fewer, 13 kilobases apart or fewer, 12 kilobases apart or fewer, 11 kilobases apart or fewer, 10 kilobases apart or fewer, 9 kilobases apart or fewer, 8 kilobases apart or fewer, 7 kilobases apart or fewer, 6 kilobases apart or fewer, 5 kilobases apart or fewer, 4 kilobases apart or fewer, 3 kilobases apart or fewer, 2 kilobases apart or fewer or 1 kilobase apart or fewer. In certain aspects, two or more high resolution Oligopaints have a resolution of about 1900 bases apart or fewer, 1800 bases apart or fewer, 1700 bases apart or fewer, 1600 bases apart or fewer, 1500 bases apart or fewer, 1400 bases apart or fewer, 1300 bases apart or fewer, 1200 bases apart or fewer, 1100 bases apart or fewer, 1000 bases apart or fewer, 900 bases apart or fewer, 800 bases apart or fewer, 700 bases apart or fewer, 600 bases apart or fewer, 500 bases apart or fewer, 400 bases apart or fewer, 300 bases apart or fewer, 200 bases apart or fewer, 100 bases apart or fewer, 95 bases apart or fewer, 90 bases apart or fewer, 85 bases apart or fewer, 80 bases apart or fewer, 75 bases apart or fewer, 70 bases apart or fewer, 65 bases apart or fewer, 60 bases apart or fewer, 55 bases apart or fewer, 50 bases apart or fewer, 45 bases apart or fewer, 40 bases apart or fewer, 35 bases apart or fewer, 30 bases apart or fewer, 25 bases apart or fewer, 20 bases apart or fewer, 15 bases apart or fewer, 10 bases apart or fewer or down to the individual base pair. In certain aspects, two or more high resolution Oligopaints have a resolution of between about 10 bases and about 2000 bases, between about 10 bases and about 1000 bases, between about 10 bases and about 500 bases, between about 15 bases and about 250 bases, between about 15 bases and about 100 bases, between about 20 bases and about 50 bases, or between about 20 bases and about 30 bases.

The sensitivity of resolution of Oligopaints described herein is much greater than paints known in the art. As used herein, the term "sensitivity," with respect to Oligopaints, refers to the number of target nucleotide bases (e.g., target genomic nucleotide bases) that are complementary to a particular Oligopaint, i.e., the number of target nucleotide bases to which a particular Oligopaint can hybridize (i.e., the smallest band size that can be detected). In certain aspects, high resolution Oligopaints have a resolution of about 1 kilobase, about 1900 bases, about 1800 bases, about 1700 bases, about 1600 bases apart, about 1500 bases, about 1400 bases, about 1300 bases, about 1200 bases, about 1100 bases, about 1000 bases, about 900 bases, about 800 bases, about 700 bases, about 600 bases, about 500 bases, about 400 bases, about 300 bases, about 200 bases, about 100 bases, about 95 bases, about 90 bases, about 85 bases, about 80 bases, about 75 bases, about 70 bases, about 65 bases, about 60 bases, about 55 bases, about 50 bases, about 45 bases, about 40 bases, about 35 bases, about 30 bases, about 25 bases, about 20 bases, about 15 bases, about 10 bases, or about 5 bases. In certain aspects, the number of target nucleotide bases that are complementary to an Oligopaint are consecutive (e.g., consecutive genomic nucleotide bases).

In certain exemplary embodiments, Oligopaints are complementary to genomic nucleic sequences that are present in low or single copy numbers (e.g., genomic nucleic sequences that are not repetitive elements). As used herein, the term "repetitive element" refers to a DNA sequence that is present in many identical or similar copies in the genome. Repetitive elements are not intended to refer to a DNA sequence that is present on each copy of the same chromosome (e.g., a DNA sequence that is present only once, but is found on both copies of chromosome 11, would not be considered a repetitive element, and would be considered a sequence that is present in the genome as one copy). The genome consists of three broad sequence components: Single copy or at least very low copy number DNA (approximately 60% of the human genome); moderately repetitive elements (approximately 30% of the human genome); and highly repetitive elements (approximately 10% of the human genome). For a review, see Human Molecular Genetics, Chapter 7 (1999), John Wiley & Sons, Inc.

In certain exemplary embodiments, small Oligopaints are provided. As used herein, the term "small Oligopaint" refers to an Oligopaint of between about 5 bases and about 100 bases long, or an Oligopaint of about 5 bases, about 10 bases, about 15 bases, about 20 bases, about 25 bases, about 30 bases, about 35 bases, about 40 bases, about 45 bases, about 50 bases, about 55 bases, about 60 bases, about 65 bases, about 70 bases, about 75 bases, about 80 bases, about 85 bases, about 90 bases, about 95 bases, or about 100 bases. Small Oligopaints can access targets that are not accessible to longer oligonucleotide probes. For example, in certain aspects small Oligopaints can pass into a cell, can pass into a nucleus, and/or can hybridize with targets that are partially bound by one or more proteins, etc. Small Oligopaints are also useful for reducing background, as they can be more easily washed away than larger hybridized oligonucleotide sequences.

In certain exemplary embodiments, the length of an Oligopaint can be increased (e.g., by primer extension) after it has been hybridized to a target sequence, e.g., a target genomic sequence. Such an extension can increase the binding affinity of the Oligopaint to the target sequence, allowing more stringent hybridization and/or wash conditions to be used (temperature, salt concentration, detergent concentration and the like, discussed further herein) as compared to a shorter Oligopaint while still allowing the use of small Oligopaints. In certain aspects, the use of stringent hybridization and/or wash conditions improves the signal to noise ratio of an Oligopaint.

As used herein, the terms "Oligopainted" and "Oligopainted region" refer to a target nucleotide sequence (e.g., a chromosome) or region of a target nucleotide sequence (e.g., a sub-chromosomal region), respectively, that has hybridized thereto one or more Oligopaints. Oligopaints can be used to label a target nucleotide sequence, e.g., chromosomes and sub-chromosomal regions of chromosomes during various phases of the cell cycle including, but not limited to, interphase, preprophase, prophase, prometaphase, metaphase, anaphase, telophase and cytokenesis.

As used herein, the term "chromosome" refers to the support for the genes carrying heredity in a living cell, including DNA, protein, RNA and other associated factors. The conventional international system for identifying and numbering the chromosomes of the human genome is used herein. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, *Homo*, *Drosophila*, *Caenorhabiditis*, *Danio*, *Cyprinus*, *Equus*, *Canis*, *Ovis*, *Ocorynchus*, *Salmo*, *Bos*, *Sus*, *Gallus*, *Solanum*, *Triticum*, *Oryza*, *Zea*, *Hordeum*, *Musa*, *Avena*, *Populus*, *Brassica*, *Saccharum* and the like.

As used herein, the term "chromosome banding" refers to differential staining of chromosomes resulting in a pattern of transverse bands of distinguishable (e.g., differently or alternately colored) regions, that is characteristic for the individual chromosome or chromosome region (i.e., the "banding pattern"). Conventional banding techniques include G-banding (Giemsa stain), Q-banding (Quinacrine mustard stain), R-banding (reverse-Giemsa), and C-banding (centromere banding).

As used herein, the term "karyotype" refers to the chromosome characteristics of an individual cell, cell line or genome of a given species, as defined by both the number and morphology of the chromosomes. Karyotype can refer to a variety of chromosomal rearrangements including, but not limited to, translocations, insertional translocations, inversions, deletions, duplications, transpositions, anueploidies, complex rearrangements, telomere loss and the like. Typically, the karyotype is presented as a systematized array of prophase or metaphase (or otherwise condensed) chromosomes from a photomicrograph or computer-generated image. Interphase chromosomes may also be examined.

As used herein, the terms "chromosomal aberration" or "chromosome abnormality" refer to a deviation between the structure of the subject chromosome or karyotype and a normal (i.e., non-aberrant) homologous chromosome or karyotype. The deviation may be of a single base pair or of many base pairs. The terms "normal" or "non-aberrant,"

when referring to chromosomes or karyotypes, refer to the karyotype or banding pattern found in healthy individuals of a particular species and gender. Chromosome abnormalities can be numerical or structural in nature, and include, but are not limited to, aneuploidy, polyploidy, inversion, translocation, deletion, duplication and the like. Chromosome abnormalities may be correlated with the presence of a pathological condition or with a predisposition to developing a pathological condition. Chromosome aberrations and/or abnormalities can also refer to changes that are not associated with a disease, disorder and/or a phenotypic change. Such aberrations and/or abnormalities can be rare or present at a low frequency (e.g., a few percent of the population (e.g., polymorphic)).

Disorders associated with one or more chromosome abnormalities include, but are not limited to: autosomal abnormalities (e.g., trisomies (Down syndrome (chromosome 21), Edwards syndrome (chromosome 18), Patau syndrome (chromosome 13), trisomy 9, Warkany syndrome (chromosome 8), trisomy 22/cat eye syndrome, trisomy 16); monosomies and/or deletions (Wolf-Hirschhorn syndrome (chromosome 4), Cri du chat/Chromosome 5q deletion syndrome (chromosome 5), Williams syndrome (chromosome 7), Jacobsen syndrome (chromosome 11), Miller-Dieker syndrome/Smith-Magenis syndrome (chromosome 17), Di George's syndrome (chromosome 22), genomic imprinting (Angelman syndrome/Prader-Willi syndrome (chromosome 15))); X/Y-linked abnormalities (e.g., monosomies (Turner syndrome (XO), trisomy or tetrasomy and/or other karyotypes or mosaics (Klinefelter's syndrome (47 (XXY)), 48 (XXYY), 48 (XXXY), 49 (XXXYY), 49 (XXXXY), Triple X syndrome (47 (XXX)), 48 (XXXX), 49 (XXXXX), 47 (XYY), 48 (XYYY), 49 (XYYYY), 46 (XX/XY)); translocations (e.g., leukemia or lymphoma (e.g., lymphoid (e.g., Burkitt's lymphoma t(8 MYC; 14 IGH), follicular lymphoma t(14 IGH; 18 BCL2), mantle cell lymphoma/multiple myeloma t(11 CCND1; 14 IGH), anaplastic large cell lymphoma t(2 ALK; 5 NPM1), acute lymphoblastic leukemia) or myeloid (e.g., Philadelphia chromosome t(9 ABL; 22 BCR), acute myeloblastic leukemia with maturation t(8 RUNX1T1; 21 RUNX1), acute promyelocytic leukemia t(15 PML, 17 RARA), acute megakaryoblastic leukemia t(1 RBM15; 22 MKL1))) or other (e.g., Ewing's sarcoma t(11 Fil1; 22 EWS), synovial sarcoma t(x SYT; 18 SSX), dermatofibrosarcoma protuberans t(17 COL1A1; 22 PDGFB), myxoid liposarcoma t(12 DDIT3; 16 FUS), desmoplastic small round cell tumor t(11 WT1; 22 EWS), alveolar rhabdomyosarcoma t(2 PAX3; 13 FOXO1) t (1 PAX7; 13 FOXO1))); gonadal dysgenesis (e.g., mixed gonadal dysgenesis, XX gonadal dysgenesis); and other abnormalities (e.g., fragile X syndrome, uniparental disomy). Disorders associated with one or more chromosome abnormalities also include, but are not limited to, Beckwith-Wiedmann syndrome, branchio-oto-renal syndrome, Cri-du-Chat syndrome, De Lange syndrome, holoprosencephaly, Rubinstein-Taybi syndrome and WAGR syndrome.

Disorders associated with one or more chromosome abnormalities also include cellular proliferative disorders (e.g., cancer). As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition, 1995). The terms "neoplasm" and "tumor" refer to an abnormal tissue that grows by cellular proliferation more rapidly than normal and continues to grow after the stimuli that initiated proliferation is removed (see, for example, PDR Medical Dictionary 1st edition, 1995). Such abnormal tissue shows partial or complete lack of structural organization and functional coordination with the normal tissue which may be either benign (i.e., benign tumor) or malignant (i.e., malignant tumor).

Disorders associated with one or more chromosome abnormalities also include brain disorders including, but not limited to, acoustic neuroma, acquired brain injury, Alzheimer's disease, amyotrophic lateral diseases, aneurism, aphasia, arteriovenous malformation, attention deficit hyperactivity disorder, autism Batten disease, Bechet's disease, blepharospasm, brain tumor, cerebral palsy Charcot-Marie-Tooth disease, chiari malformation, CIDP, non-Alzheimer-type dementia, dysautonomia, dyslexia, dysprazia, dystonia, epilepsy, essential tremor, Friedrich's ataxia, gaucher disease, Gullian-Barre syndrome, headache, migraine, Huntington's disease, hydrocephalus, Meniere's disease, motor neuron disease, multiple sclerosis, muscular dystrophy, myasthenia gravis, narcolepsy, Parkinson's disease, peripheral neuropathy, progressive supranuclear palsy, restless legs syndrome, Rett syndrome, schizophrenia, Shy Drager syndrome, stroke, subarachnoid hemorrhage, Sydenham's syndrome, Tay-Sachs disease, Tourett syndrome, transient ischemic attack, transverse myelitis, trigeminal neuralgia, tuberous sclerosis and von Hippel-Lindau syndrome.

In certain exemplary embodiments, Oligopaint kits are provided. As used herein, the term "kit" refers to any delivery system for delivering Oligopaints and/or reagents for carrying out a method described herein. In the context of assays, such kits include systems that allow for the storage, transport, or delivery of reaction reagents (e.g., an enclosure providing one or more of, e.g., Oligopaints, primers (e.g., primers specific for all Oligopaints present and/or one or more subsets of primers specific to one or more subsets of Oligopaint sequences) primers having one or more detectable and/or retrievable labels bound thereto), supports having oligonucleotides bound thereto (e.g., microarrays, palettes, etc.), or the like) and/or supporting materials (e.g., an enclosure providing, e.g., buffers, written instructions for performing an assay described herein, or the like) from one location to another. For example, kits include one or more enclosures (e.g., boxes) containing the relevant reaction reagents and/or supporting materials for assays described herein. In one aspect, kits of the invention comprise Oligopaints specific for one or more target nucleotide sequences (e.g., chromosomes) or one or more regions of one or more target nucleotide sequences (e.g., sub-chromosomal regions). In another aspect, kits comprise one or more primer sequences, one or more supports having a plurality of synthetic, oligonucleotide sequences attached thereto, and one or more detectable and/or retrievable labels. Such contents may be delivered to the intended recipient together or separately. For example, a first container may contain primer sequences for use in an assay, while a second container may contain a support having a plurality of synthetic, oligonucleotide sequences attached thereto.

In certain embodiments, an Oligopaint kit provides one or more arrays and/or palettes having a plurality of specific oligonucleotide sequences (e.g., Oligopaints) bound thereto. In certain aspects, an array and/or palette provides a plurality of oligonucleotide sequences (e.g., Oligopaints) that is specific for a set of binding patterns in a genome (e.g., a human genome). In certain aspects, an array or palette is specific for a set of chromosomal aberrations (e.g., one or more of a translocation, an insertion, an inversion, a deletion, a duplication, a transposition, aneuploidy, polyploidy, complex rearrangement and telomere loss) associated with one or more disorders described herein. In certain aspects, the Oligopaint kits described herein are particularly suited for diagnostic and/or prognostic use for detecting one or more disorders described herein in clinical settings (e.g., hospitals, medical clinics, medical offices, diagnostic laboratories, research laboratories and the like (e.g., for patient diagnosis and/or prognosis, prenatal diagnosis and/or prognosis and the like).

In certain aspects, an Oligopaint kit provides instructions for amplifying the plurality of specific oligonucleotide sequences (e.g., Oligopaints) provided in the kit. In other aspects, the kit provides instructions for detectably and/or retrievably labeling one or more target nucleic acid sequences (e.g., one or more chromosomes or sub-chromosomal regions) using the amplified Oligopaints. In other aspects, an Oligopaint kit provides instructions for effectively removing one or more of the plurality of specific oligonucleotide sequences (e.g., Oligopaints) during the amplification step by including one or more unlabeled amplification primers that hybridizes to the one or more oligonucleotide sequences that one wishes to remove, such that the one or more target nucleic acid sequences is rendered not detectably and/or retrievably labeled.

In certain exemplary embodiments, a polynucleotide (e.g., an Oligopaint) has a retrievable label bound thereto. As used herein, the terms "bound" and "attached" refer to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994.

As used herein, the term "retrievable label" refers to a label that is attached to a polynucleotide (e.g., an Oligopaint) and can, optionally, be used to specifically and/or nonspecifically bind a target protein, peptide, DNA sequence, RNA sequence, carbohydrate or the like at or near the nucleotide sequence to which one or more Oligopaints have hybridized. In certain aspects, target proteins include, but are not limited to, proteins that are involved with gene regulation such as, e.g., proteins associated with chromatin (See, e.g., Dejardin and Kingston (2009) *Cell* 136:175), proteins that regulate (upregulate or downregulate) methylation, proteins that regulate (upregulate or downregulate) histone acetylation, proteins that regulate (upregulate or downregulate) transcription, proteins that regulate (upregulate or downregulate) post-transcriptional regulation, proteins that regulate (upregulate or downregulate) RNA transport, proteins that regulate (upregulate or downregulate) mRNA degradation, proteins that regulate (upregulate or downregulate) translation, proteins that regulate (upregulate or downregulate) post-translational modifications and the like.

In certain aspects, a retrievable label is activatable. As used herein, the term "activatable" refers to a retrievable label that is inert (i.e., does not bind a target) until activated (e.g., by exposure of the activatable, retrievable label to light, heat, one or more chemical compounds or the like). In other aspects, a retrievable label can bind one or more targets without the need for activation of the retrievable label.

In certain exemplary embodiments, a polynucleotide (e.g., an Oligopaint) has a detectable label bound thereto. As used herein, the term "detectable label" refers to a label that is attached to a polynucleotide (e.g., an Oligopaint) and can be used to identify a target (e.g., a chromosome or a sub-chromosomal region) to which one or more Oligopaints have hybridized. Typically, a detectable label is attached to the 3'- or 5'-end of a polynucleotide (e.g., an Oligopaint). Alternatively, a detectable label is attached to an internal portion of an oligonucleotide (i.e., not at the 3' or the 5' end). Detectable labels may vary widely in size and compositions; the following references provide guidance for selecting oligonucleotide tags appropriate for particular embodiments: Brenner, U.S. Pat. No. 5,635,400; Brenner et al., *Proc. Natl. Acad. Sci.*, 97: 1665; Shoemaker et al. (1996) *Nature Genetics*, 14:450; Morris et al., EP Patent Pub. 0799897A1; Wallace, U.S. Pat. No. 5,981,179; and the like.

In certain exemplary embodiments, a polynucleotide (e.g., an Oligopaint) including one or more detectable labels can have a length within a range of from 4 to 36 nucleotides, or from 6 to 30 nucleotides, or from 8 to 20 nucleotides, respectively. In other exemplary embodiments a polynucleotide (e.g., an Oligopaint) including one or more detectable labels can have a length of at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 150 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides or greater.

Methods for incorporating detectable labels into nucleic acid probes are well known. Typically, detectable labels (e.g., as hapten- or fluorochrome-conjugated deoxyribonucleotides) are incorporated into an oligopaint during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

In certain aspects, a suitable retrievable label or detectable label includes, but is not limited to, a capture moiety such as a hydrophobic compound, an oligonucleotide, an antibody or fragment of an antibody, a protein, a peptide, a chemical cross-linker, an intercalator, a molecular cage (e.g., within a cage or other structure, e.g., protein cages, fullerene cages, zeolite cages, photon cages, and the like), or one or more elements of a capture pair, e.g., biotin-avidin, biotin-streptavidin, NHS-ester and the like, a thioether linkage, static charge interactions, van der Waals forces and the like (See, e.g., Holtke et al., U.S. Pat. Nos. 5,344,757; 5,702,888; and 5,354,657; Huber et al., U.S. Pat. No. 5,198,537; Miyoshi, U.S. Pat. No. 4,849,336; Misiura and Gait, PCT publication WO 91/17160). In certain aspects, a suitable retrievable label or detectable label is an enzyme (e.g., a methylase and/or a cleaving enzyme). In one aspect, an antibody specific against the enzyme can be used to retrieve or detect the enzyme and accordingly, retrieve or detect an oligonucleotide sequence attached to the enzyme. In another aspect, an antibody specific against the enzyme can be used to retrieve or detect the enzyme and, after stringent washes, retrieve or detect an first oligonucleotide sequence that is hybridized to a second oligonucleotide sequence having the enzyme attached thereto.

Biotin, or a derivative thereof, may be used as an oligonucleotide (e.g., Oligopaint) label (e.g., as a retrievable label and/or a detectable label), and subsequently bound by a avidin/streptavidin derivative (e.g., detectably labeled, e.g., phycoerythrin-conjugated streptavidin), or an anti-biotin antibody (e.g., a detectably labeled antibody). Digoxigenin may be incorporated as a label and subsequently bound by a detectably labeled anti-digoxigenin antibody (e.g., a detectably labeled antibody, e.g., fluoresceinated anti-digoxigenin). An aminoallyl-dUTP residue may be incorporated into an oligonucleotide and subsequently coupled to an N-hydroxy succinimide (NHS) derivatized fluorescent dye, such as those listed infra. In general, any member of a conjugate pair may be incorporated into a retrievable label and/or a detectable label provided that a detectably labeled conjugate partner can be bound to permit detection. As used herein, the term antibody refers to an antibody molecule of any class, or any sub-fragment thereof, such as an Fab.

Other suitable labels (retrievable labels and/or detectable labels) include, but are not limited to, fluorescein (FAM), digoxigenin, dinitrophenol (DNP), dansyl, biotin, bromodeoxyuridine (BrdU), hexahistidine (6xHis), phosphor-amino acids (e.g. P-tyr, P-ser, P-thr) and the like. In one embodiment the following hapten/antibody pairs are used for retrieval and/or detection: biotin/α-biotin, digoxigenin/a-digoxigenin, dinitrophenol (DNP)/α-DNP, 5-Carboxyfluorescein (FAM)/α-FAM.

Additional suitable labels (retrievable labels and/or detectable labels) include, but are not limited to, chemical cross-linking agents. Cross-linking agents typically contain at least two reactive groups that are reactive towards numerous groups, including, but not limited to, sulfhydryls and amines, and create chemical covalent bonds between two or more molecules. Functional groups that can be targeted with cross-linking agents include, but are not limited to, primary amines, carboxyls, sulfhydryls, carbohydrates and carboxylic acids. Protein molecules have many of these functional groups and therefore proteins and peptides can be readily conjugated using cross-linking agents. Cross-linking agents are well known in the art and are commercially available (Thermo Scientific (Rockford, Ill.)).

Fluorescent labels and their attachment to oligonucleotides (e.g., to Oligopaints) are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); Wetmur, *Critical Reviews in Biochemistry and Molecular Biology*, 26:227-259 (1991); and the like. Particular methodologies applicable to the Oligopaint methods and compositions described herein are disclosed in the following sample of references: Fung et al., U.S. Pat. No. 4,757,141; Hobbs, Jr., et al. U.S. Pat. No. 5,151,507; Cruickshank, U.S. Pat. No. 5,091,519. In one embodiment, one or more fluorescent dyes are used as labels for Oligopaints, e.g., as disclosed by Menchen et al., U.S. Pat. No. 5,188,934 (4,7-dichlorofluorscein dyes); Begot et al., U.S. Pat. No. 5,366,860 (spectrally resolvable rhodamine dyes); Lee et al., U.S. Pat. No. 5,847,162 (4,7-dichlororhodamine dyes); Khanna et al., U.S. Pat. No. 4,318,846 (ether-substituted fluorescein dyes); Lee et al., U.S. Pat. No. 5,800,996 (energy transfer dyes); Lee et al., U.S. Pat. No. 5,066,580 (xanthine dyes): Mathies et al., U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. Amines can be incorporated into Oligopaints, and labels can be added via the amines using methods known in the art. As used herein, the term "fluorescent label" includes a signaling moiety that conveys information through the fluorescent absorption and/or emission properties of one or more molecules. Such fluorescent properties include fluorescence intensity, fluorescence life time, emission spectrum characteristics, energy transfer and the like.

Commercially available fluorescent nucleotide analogues readily incorporated into the Oligopaints include, for example, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHODAMINE GREEN™-5-UTP, ALEXA FLUOR™ 488-5-UTP, ALEXA FLUOR™ 546-14-UTP (Molecular Probes, Inc. Eugene, Oreg.). Protocols are available for custom synthesis of nucleotides having other fluorophores. Henegariu et al., "Custom Fluorescent-Nucleotide Synthesis as an Alternative Method for Nucleic Acid Labeling," *Nature Biotechnol.* 18:345-348 (2000).

Other fluorophores available for post-synthetic attachment include, inter alia, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like) (available from Thermo Fisher Scientific, Rockford, Ill.), Texas Red (available from Molecular Probes, Inc., Eugene, Oreg.), and Cy2, Cy3.5, Cy5.5, and Cy7 (available from Amersham Biosciences, Piscataway, N.J. USA, and others).

FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

Metallic silver particles may be coated onto the surface of the array to enhance signal from fluorescently labeled oligonucleotide sequences bound to an array. Lakowicz et al. (2003) *BioTechniques* 34:62.

Detection method(s) used will depend on the particular detectable labels used in the Oligopaints. In certain exemplary embodiments, chromosomes and/or chromosomal regions having one or more Oligopaints bound thereto may be selected for and/or screened for using a microscope, a spectrophotometer, a tube luminometer or plate luminometer, x-ray film, a scintillator, a fluorescence activated cell sorting (FACS) apparatus, a microfluidics apparatus or the like.

When fluorescently labeled Oligopaints are used, fluorescence photomicroscopy can be used to detect and record the results of in situ hybridization using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular probes) for a review of methods for painting chromosomes and detecting painted chromosomes.

In certain exemplary embodiments, images of fluorescently labeled chromosomes are detected and recorded using a computerized imaging system such as the Applied Imaging Corporation CytoVision System (Applied Imaging Corporation, Santa Clara, Calif.) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al. (1992) *Proc. Natl. Acad. Sci. USA* 89:1388). Other suitable imaging and analysis systems are described by Schrock et al., supra; and Speicher et al., supra.

The in situ hybridization methods described herein can be performed on a variety of biological or clinical samples, in cells that are in any (or all) stage(s) of the cell cycle (e.g., mitosis, meiosis, interphase, G0, G1, S and/or G2). Examples include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. Samples are prepared for assays of the invention using conventional techniques, which typically depend on the source from which a sample or specimen is taken. These examples are not to be construed as limiting the sample types applicable to the methods and/or compositions described herein.

In certain exemplary embodiments, Oligopaints include multiple chromosome-specific probes, which are differentially labeled (i.e., at least two of the chromosome-specific probes are differently labeled). Various approaches to multi-color chromosome painting have been described in the art and can be adapted to the present invention following the guidance provided herein. Examples of such differential labeling ("multicolor FISH") include those described by Schrock et al. (1996) *Science* 273:494, and Speicher et al. (1996) *Nature Genet.* 12:368). Schrock et al. describes a spectral imaging method, in which epifluorescence filter sets and computer software is used to detect and discriminate between multiple differently labeled DNA probes hybridized simultaneously to a target chromosome set. Speicher et al. describes using different combinations of 5 fluorochromes to label each of the human chromosomes (or chromosome arms) in a 27-color FISH termed "combinatorial multifluor FISH"). Other suitable methods may also be used (see, e.g., Ried et al., 1992, *Proc. Natl. Acad. Sci. USA* 89:1388-92).

Hybridization of the Oligopaints of the invention to target chromosomes sequences can be accomplished by standard in situ hybridization (ISH) techniques (see, e.g., Gall and Pardue (1981) *Meth. Enzymol.* 21:470; Henderson (1982) *Int. Review of Cytology* 76:1). Generally, ISH comprises the following major steps: (1) fixation of the biological structure to be analyzed (e.g., a chromosome spread), (2) pre-hybridization treatment of the biological structure to increase accessibility of target DNA (e.g., denaturation with heat or alkali), (3) optional pre-hybridization treatment to reduce nonspecific binding (e.g., by blocking the hybridization capacity of repetitive sequences), (4) hybridization of the mixture of nucleic acids to the nucleic acid in the biological structure or tissue; (5) post-hybridization washes to remove nucleic acid fragments not bound in the hybridization and (6) detection of the hybridized labelled oligonucleotides (e.g., hybridized Oligopaints). The reagents used in each of these steps and their conditions of use vary depending on the particular situation. For instance, step 3 will not always be necessary as the Oligopaints described herein can be designed to avoid repetitive sequences). Hybridization conditions are also described in U.S. Pat. No. 5,447,841. It will be appreciated that numerous variations of in situ hybridization protocols and conditions are known and may be used in conjunction with the present invention by practitioners following the guidance provided herein.

As used herein, the term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* 1$^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

In certain exemplary embodiments, synthesis of oligonucleotides (e.g., Oligopaints) and/or amplification of oligonucleotides (e.g., Oligopaints) can be performed using a support. In certain aspects, multiple supports (tens, hundreds, thousands or more) may be utilized (e.g., synthesized, amplified, hybridized or the like) in parallel. Suitable supports include, but are not limited to, slides (e.g., microscope slides), beads, chips, particles, strands, gels, sheets, tubing (e.g., microfuge tubes, test tubes, cuvettes), spheres, containers, capillaries, microfibers, pads, slices, films, plates (e.g., multi-well plates), microfluidic supports (e.g., microarray chips, flow channel plates, biochips and the like) and the like. In various embodiments, the solid supports may be biological, nonbiological, organic, inorganic or combinations thereof. When using supports that are substantially planar, the support may be physically separated into regions, for example, with trenches, grooves, wells, or chemical barriers (e.g., lacking a lipid-binding coating). In exemplary embodiments, supports can be made of a variety of materials including, but not limited to glass, quartz, ceramic, plastic, polystyrene, methylstyrene, acrylic polymers, titanium, latex, sepharose, cellulose, nylon and the like and any combination thereof. Such supports and their uses are well known in the art.

In certain exemplary embodiments, supports may have functional groups on their surface which can be used to attach a lipid bilayer (e.g., a phospholipid bilayer) to the support. For example, at least a portion of the support can be coated with silane and dextran (e.g., high molecular weight dextran). Dextran in its hydrated form can function as a molecular cushion for the membrane and is capable of binding lipids on the support. Suitable functional groups include, but are not limited to, silicon oxides (e.g., $SiO_2$), $MgF_2$, $CaF_2$, mica, polyacrylamide, dextran and the like and any combination thereof.

In certain exemplary embodiments, methods of generating and amplifying synthetic oligonucleotide sequences, e.g., Oligopaint sequences, are provided. As used herein, the term "oligonucleotide" is intended to include, but is not limited to, a single-stranded DNA or RNA molecule, typically prepared by synthetic means. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, *Biochemistry*, Third Ed. (1988), incorporated herein by reference in its entirety for all purposes). As used herein, the term "polynucleotide" is intended to include, but is not limited to, two or more oligonucleotides joined together (e.g., by hybridization, ligation, polymerization and the like).

The term "operably linked," when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

In certain exemplary embodiments, nucleotide analogs or derivatives will be used, such as nucleosides or nucleotides having protecting groups on either the base portion or sugar portion of the molecule, or having attached or incorporated labels, or isosteric replacements which result in monomers that behave in either a synthetic or physiological environment in a manner similar to the parent monomer. The nucleotides can have a protecting group which is linked to, and masks, a reactive group on the nucleotide. A variety of protecting groups are useful in the invention and can be selected depending on the synthesis techniques employed and are discussed further below. After the nucleotide is attached to the support or growing nucleic acid, the protecting group can be removed.

Oligonucleotides or fragments thereof may be purchased from commercial sources. Oligonucleotide sequences may be prepared by any suitable method, e.g., the phosphoramidite method described by Beaucage and Carruthers ((1981) *Tetrahedron Lett.* 22: 1859) or the triester method according to Matteucci et al. (1981) *J. Am. Chem. Soc.* 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides and chips containing oligonucleotides may also be obtained commercially from a variety of vendors.

In an exemplary embodiment, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single stranded DNA molecule of desired sequence. An exemplary type of instrument is the type shown in FIG. 5 of U.S. Pat. No. 6,375,903, based on the use of reflective optics. It is a desirable that this type of maskless array synthesizer is under software control. Since the entire process of microarray synthesis can be accomplished in only a few hours, and since suitable software permits the desired DNA sequences to be altered at will, this class of device makes it possible to fabricate microarrays including DNA segments of different sequence every day or even multiple times per day on one instrument. The differences in DNA sequence of the DNA segments in the microarray can also be slight or dramatic, it makes no difference to the process. The MAS instrument may be used in the form it would normally be used to make microarrays for hybridization experiments, but it may also be adapted to have features specifically adapted for the compositions, methods, and systems described herein. For example, it may be desirable to substitute a coherent light source, i.e., a laser, for the light source shown in FIG. 5 of the above-mentioned U.S. Pat. No. 6,375,903. If a laser is used as the light source, a beam expanded and scatter plate may be used after the laser to transform the narrow light beam from the laser into a broader light source to illuminate the micromirror arrays used in the maskless array synthesizer. It is also envisioned that changes may be made to the flow cell in which the microarray is synthesized. In particular, it is envisioned that the flow cell can be compartmentalized, with linear rows of array elements being in fluid communication with each other by a common fluid channel, but each channel being separated from adjacent channels associated with neighboring rows of array elements. During microarray synthesis, the channels all receive the same fluids at the same time. After the DNA segments are separated from the substrate, the channels serve to permit the DNA segments from the row of array elements to congregate with each other and begin to self-assemble by hybridization.

Other methods for synthesizing oligonucleotides (e.g., Oligopaints) include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be used as necessary. Other applicable methods include mechanical techniques such as those described in U.S. Pat. No. 5,384,261.

Additional methods applicable to synthesis and/or amplification of oligonucleotides (e.g., Oligopaints) on a single support are described, for example, in U.S. Pat. No. 5,384,261. For example reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites.

Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. One of skill in the art will recognize that there are alternative methods of forming channels or otherwise protecting a portion of the surface of the support. For example, a protective coating such as a hydrophilic or hydrophobic coating (depending upon the nature of the solvent) is utilized over portions of the support to be protected, sometimes in combination with materials that facilitate wetting by the reactant solution in other regions. In this manner, the flowing solutions are further prevented from passing outside of their designated flow paths.

Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Typical dispensers include a micropipette to deliver the monomer solution to the support and a robotic system to control the position of the micropipette with respect to the support, or an ink-jet printer. In other embodiments, the dispenser includes a series of tubes, a manifold, an array of pipettes, or the like so that various reagents can be delivered to the reaction regions simultaneously.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtitre dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In yet another embodiment, a plurality of oligonucleotides (e.g., Oligopaints) may be synthesized on multiple supports. One example is a bead based synthesis method which is described, for example, in U.S. Pat. Nos. 5,770,358, 5,639,603, and 5,541,061. For the synthesis of molecules such as oligonucleotides on beads, a large plurality of beads are suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In certain embodiments, a plurality of oligonucleotides (e.g., Oligopaints) may be synthesized, amplified and/or used in conjunction with beads and/or bead-based arrays. As used herein, the term "bead" refers to a discrete particle that may be spherical (e.g., microspheres) or have an irregular shape. Beads may be as small as approximately 0.1 µm in diameter or as large approximately several millimeters in diameter. Beads typically range in size from approximately 0.1 µm to 200 µm in diameter. Beads may comprise a variety of materials including, but not limited to, paramagnetic materials, ceramic, plastic, glass, polystyrene, methylstyrene, acrylic polymers, titanium, latex, sepharose, cellulose, nylon and the like.

In certain aspects, beads may have functional groups on their surface which can be used to oligonucleotides (e.g., Oligopaints) to the bead. Oligonucleotide sequences can be attached to a bead by hybridization (e.g., binding to a polymer), covalent attachment, magnetic attachment, affinity attachment and the like. For example, the bead can be coated with streptavidin and the nucleic acid sequence can include a biotin moiety. The biotin is capable of binding streptavidin on the bead, thus attaching the nucleic acid sequence to the bead. Beads coated with streptavidin, oligo-dT, and histidine tag binding substrate are commercially available (Dynal Biotech, Brown Deer, Wis.). Beads may also be functionalized using, for example, solid-phase chemistries known in the art, such as those for generating nucleic acid arrays, such as carboxyl, amino, and hydroxyl groups, or functionalized silicon compounds (see, for example, U.S. Pat. No. 5,919,523).

Various exemplary protecting groups useful for synthesis of oligonucleotides on a solid support are described in, for example, Atherton et al., 1989, Solid Phase Peptide Synthesis, IRL Press. In various embodiments, the methods described herein utilize solid supports for immobilization of nucleic acids. For example, oligonucleotides may be synthesized on one or more solid supports. Exemplary solid supports include, for example, slides, beads, chips, particles, strands, gels, sheets, tubing, spheres, containers, capillaries, pads, slices, films, or plates. In various embodiments, the solid supports may be biological, nonbiological, organic, inorganic, or combinations thereof. When using supports that are substantially planar, the support may be physically separated into regions, for example, with trenches, grooves, wells, or chemical barriers (e.g., hydrophobic coatings, etc.). Supports that are transparent to light are useful when the assay involves optical detection (see e.g., U.S. Pat. No. 5,545,531). The surface of the solid support will typically contain reactive groups, such as carboxyl, amino, and hydroxyl or may be coated with functionalized silicon compounds (see e.g., U.S. Pat. No. 5,919,523).

In one embodiment, the oligonucleotides synthesized on the solid support may be used as a template for the production of Oligopaints. For example, the support bound oligonucleotides may be contacted with primers that hybridize to the oligonucleotides under conditions that permit chain extension of the primers. The support bound duplexes may then be denatured, pooled and subjected to further rounds of amplification to produce Oligopaints in solution. In another embodiment, the support-bound oligonucleotides may be removed from the solid, pooled and amplified to produce Oligopaints in solution. The oligonucleotides may be removed from the solid support, for example, by exposure to conditions such as acid, base, oxidation, reduction, heat, light, metal ion catalysis, displacement or elimination chemistry, or by enzymatic cleavage.

In one embodiment, oligonucleotides may be attached to a solid support through a cleavable linkage moiety. For example, the solid support may be functionalized to provide cleavable linkers for covalent attachment to the oligonucleotides. The linker moiety may be one, two, three, four, five, six or more atoms in length. Alternatively, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., Ann. Rev. Biochem. 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of solid support, and/or the mode of reagent delivery, among others. In an exemplary embodiment, the oligonucleotides cleaved from the solid support contain a free 3'-OH end. Alternatively, the free 3'-OH end may also be obtained by chemical or enzymatic treatment, following the cleavage of oligonucleotides. The cleavable moiety may be removed under conditions which do not degrade the oligonucleotides. The linker may be cleaved using two approaches, either (a) simultaneously under the same conditions as the deprotection step or (b) subsequently utilizing a different condition or reagent for linker cleavage after the completion of the deprotection step.

The covalent immobilization site may either be at the 5' end of the oligonucleotide or at the 3' end of the oligonucleotide. In some instances, the immobilization site may be within the oligonucleotide (i.e. at a site other than the 5' or 3' end of the oligonucleotide). The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

In one embodiment, cleavable sites contained within the modified oligonucleotide may include chemically cleavable groups, such as dialkoxysilane, 3'-(S)-phosphorothioate, 5'-(S)-phosphorothioate, 3'-(N)-phosphoramidate, 5'-(N)phosphoramidate, and ribose. Synthesis and cleavage conditions of chemically cleavable oligonucleotides are described in U.S. Pat. Nos. 5,700,642 and 5,830,655. For example, depending upon the choice of cleavable site to be introduced, either a functionalized nucleoside or a modified nucleoside dimer may be first prepared, and then selectively introduced into a growing oligonucleotide fragment during the course of oligonucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide.

In another embodiment, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of the oligonucleotide synthesis yields an oligonucleotide bearing a phosphate group at the 3' end. The 3'-phosphate end may be converted to a 3' hydroxyl end by a treatment with a chemical or an enzyme, such as alkaline phosphatase, which is routinely carried out by those skilled in the art.

In another embodiment, the cleavable linking moiety may be a TOPS (two oligonucleotides per synthesis) linker (see e.g., PCT publication WO 93/20092). For example, the TOPS phosphoramidite may be used to convert a non-cleavable hydroxyl group on the solid support to a cleavable linker. A preferred embodiment of TOPS reagents is the Universal TOPS™ phosphoramidite. Conditions for Universal TOPS™ phosphoramidite preparation, coupling and cleavage are detailed, for example, in Hardy et al, Nucleic Acids Research 22(15):2998-3004 (1994). The Universal TOPS™ phosphoramidite yields a cyclic 3' phosphate that may be removed under basic conditions, such as the extended ammonia and/or ammonia/methylamine treatment, resulting in the natural 3' hydroxy oligonucleotide.

In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide.

In another embodiment, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al. J. of Org. Chem. 61:525-529 (1996), Kahl et al., J. of Org. Chem. 64:507-510 (1999), Kahl et al., J. of Org. Chem. 63:4870-4871 (1998), Greenberg et al., J. of Org. Chem. 59:746-753 (1994), Holmes et al., J. of Org. Chem. 62:2370-2380 (1997), and U.S. Pat. No. 5,739,386. Ortho-nitobenzyl-based linkers, such as hydroxymethyl, hydroxyethyl, and Fmoc-aminoethyl carboxylic acid linkers, may also be obtained commercially.

In another embodiment, oligonucleotides may be removed from a solid support by an enzyme such as a nuclease. For example, oligonucleotides may be removed from a solid support upon exposure to one or more restriction endonucleases, including, for example, class IIs restriction enzymes. A restriction endonuclease recognition sequence may be incorporated into the immobilized oligonucleotides and the oligonucleotides may be contacted with one or more restriction endonucleases to remove the oligonucleotides from the support. In various embodiments, when using enzymatic cleavage to remove the oligonucleotides from the support, it may be desirable to contact the single stranded immobilized oligonucleotides with primers, polymerase and dNTPs to form immobilized duplexes. The duplexes may then be contacted with the enzyme (e.g., a restriction endonuclease) to remove the duplexes from the surface of the support. Methods for synthesizing a second strand on a support bound oligonucleotide and methods for enzymatic removal of support bound duplexes are described, for example, in U.S. Pat. No. 6,326,489. Alternatively, short oligonucleotides that are complementary to the restriction endonuclease recognition and/or cleavage site (e.g., but are not complementary to the entire support bound oligonucleotide) may be added to the support bound oligonucleotides under hybridization conditions to facilitate cleavage by a restriction endonuclease (see e.g., PCT Publication No. WO 04/024886).

In yet another embodiment, a plurality of oligonucleotides (e.g., Oligopaints) may be synthesized and/or amplified in solution. Methods of synthesizing oligonucleotide sequences are well-known in the art (See, e.g., Seliger (1993) *Protocols for Oligonucleotides and Analogs: Synthesis and Properties*, vol. 20, pp. 391-435, Efimov (2007) *Nucleosides, Nucleotides & Nucleic Acids* 26:8, McMinn et al. (1997) *J. Org. Chem.* 62:7074, Froehler et al. (1986) *Nucleic Acids Res.* 14:5399, Garegg (1986) *Tet. Lett.* 27:4051, Efimov (1983) *Nucleic Acids Res.* 11:8369, Reese (1978) *Tetrahedron* 34:3143).

In certain embodiments, oligonucleotides (e.g., Oligopaints) are double stranded (ds). In certain aspects, a ds oligonucleotide may be synthesized as two single stranded oligonucleotides that are hybridized together, thus forming a ds oligonucleotide. Alternatively, a ds oligonucleotide may be synthesized is a ds form (e.g., using a ss oligonucleotide as a template). In other embodiments, oligonucleotides (e.g., Oligopaints) are single stranded (ss). In certain aspects, a ss oligonucleotide is generated in a ss form. In other aspects, a ss oligonucleotide is synthesized in a ds form and is converted to ss form subsequent to synthesis using any of a variety of methods well known in the art (e.g., by incorporating dUs into the ds oligonucleotide during synthesis that can be cleaved after synthesis, by chemical cleavage after synthesis, by enzymatic cleavage after synthesis, by nuclease digestion after synthesis, by light based cleavage after synthesis and the like).

Exemplary chemically cleavable internucleotide linkages for use in the methods described herein include, for example, β-cyano ether, 5'-deoxy-5'-aminocarbamate, 3'deoxy-3'-aminocarbamate, urea, 2'cyano-3',5'-phosphodiester, 3'-(S)-phosphorothioate, 5'-(S)-phosphorothioate, 3'-(N)-phosphoramidate, 5'-(N)-phosphoramidate, a-amino amide, vicinal diol, ribonucleoside insertion, 2'-amino-3',5'-phosphodiester, allylic sulfoxide, ester, silyl ether, dithioacetal, 5'-thio-furmal, α-hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include β-cyano ether, 5'-deoxy-5'-aminocarbamate, 3'-deoxy-3'-aminocarbamate, urea, 2'-cyano-3', 5'-phosphodiester, 2'-amino-3', 5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An α-aminoamide internucleoside bond is cleavable by treatment with isothiocyanate, and titanium may be used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642.

Enzymatic cleavage may be mediated by including a restriction endonuclease cleavage site in the oligonucleotide sequence. After synthesis of a ds oligonucleotide, the ds oligonucleotide may be contacted with one or more endonucleases to remove one strand. A wide variety of restriction endonucleases having specific binding and/or cleavage sites are commercially available, for example, from New England Biolabs (Ipswich, Mass.).

In various embodiments, the methods disclosed herein comprise amplification of oligonucleotide sequences including, for example, Oligopaints. Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, universal primers will be used to amplify nucleic acid sequences such as, for example, Oligopaints. The term "universal primers" refers to a set of primers (e.g., a forward and reverse primer) that may be used for chain extension/amplification of a plurality of polynucleotides, e.g., the primers hybridize to sites that are common to a plurality of polynucleotides. For example, universal primers may be used for amplification of all, or essentially all, polynucleotides in a single pool. In certain aspects, forward primers and reverse primers have the same sequence. In other aspects, the sequence of forward primers differs from the sequence of reverse primers. In still other aspects, a plurality of universal primers are provided, e.g., tens, hundreds, thousands or more.

In certain embodiments, the universal primers may be temporary primers that may be removed after amplification via enzymatic or chemical cleavage. In certain embodiments, the universal primers may be temporary primers that may be removed after amplification via enzymatic or chemical cleavage. In other embodiments, the universal primers may comprise a modification that becomes incorporated into the polynucleotide molecules upon chain extension. Exemplary modifications include, for example, a 3' or 5' end cap, a label (e.g., fluorescein), or a tag (e.g., a tag that facilitates immobilization or isolation of the polynucleotide, such as, biotin, etc.).

In exemplary embodiments, primers may be designed to be temporary to permit removal of the primers. Temporary primers may be designed so as to be removable by chemical, thermal, light based, or enzymatic cleavage. Cleavage may occur upon addition of an external factor (e.g., an enzyme, chemical, heat, light, etc.) or may occur automatically after a certain time period (e.g., after n rounds of amplification). In one embodiment, temporary primers may be removed by chemical cleavage. For example, primers having acid labile or base labile sites may be used for amplification. The amplified pool may then be exposed to acid or base to remove the primer at the desired location. Alternatively, the temporary primers may be removed by exposure to heat and/or light. For example, primers having heat labile or photolabile sites may be used for amplification. The amplified pool may then be exposed to heat and/or light to remove the primer/primer binding sites at the desired location. In another embodiment, an RNA primer may be used for amplification thereby forming short stretches of RNA/DNA hybrids at the ends of the nucleic acid molecule. The primer site may then be removed by exposure to an RNase (e.g., RNase H). In various embodiments, the method for removing the primer may only cleave a single strand of the amplified duplex thereby leaving 3' or 5' overhangs. Such overhangs may be removed using an exonuclease to form blunt ended double stranded duplexes. For example, RecJ$_f$ may be used to remove single stranded 5' overhangs and Exonuclease I or Exonuclease T may be used to remove single stranded 3' overhangs. Additionally, S$_1$ nuclease, P$_1$ nuclease, mung bean nuclease, and CEL I nuclease, may be used to remove single stranded regions from a nucleic acid molecule. RecJ$_f$, Exonuclease I, Exonuclease T, and mung bean nuclease are commercially available, for example, from New England Biolabs (Ipswich, Mass.). S1 nuclease, P1 nuclease and CEL I nuclease are described, for example, in Vogt, V. M., *Eur. J. Biochem.*, 33: 192-200 (1973); Fujimoto et al., *Agric. Biol. Chem.* 38: 777-783 (1974); Vogt, V. M., *Methods Enzymol.* 65: 248-255 (1980); and Yang et al., *Biochemistry* 39: 3533-3541 (2000).

In one embodiment, the temporary primers may be removed from a nucleic acid by chemical, thermal, or light based cleavage as described supra. In other embodiments, primers may be removed using enzymatic cleavage. For example, primers may be designed to include a restriction endonuclease cleavage site. After amplification, the pool of nucleic acids may be contacted with one or more endonucleases to produce double stranded breaks thereby removing the primers. In certain embodiments, the forward and reverse primers may be removed by the same or different restriction endonucleases. Any type of restriction endonuclease may be used to remove the primers/primer binding sites from nucleic acid sequences. In various embodiments, restriction endonucleases that produce 3' overhangs, 5' overhangs or blunt ends may be used.

In certain embodiments, it may be desirable to utilize a primer comprising one or more modifications such as a cap (e.g., to prevent exonuclease cleavage), a linking moiety (such as those described above to facilitate immobilization of an oligonucleotide onto a substrate), or a label (e.g., to facilitate detection, isolation and/or immobilization of a nucleic acid construct). Suitable modifications include, for example, various enzymes, prosthetic groups, luminescent markers, bioluminescent markers, fluorescent markers (e.g., fluorescein), radiolabels (e.g., $^{32}$P, $^{35}$S, etc.), biotin, polypeptide epitopes, etc. as described further herein.

Embodiments of the present invention are directed to oligonucleotide sequences (e.g., Oligopaints) having one or more amplification sequences or amplification sites. As used herein, the term "amplification site" is intended to include, but is not limited to, a nucleic acid sequence located at the 5' and/or 3' end of the oligonucleotide sequences of the present invention which hybridizes a complementary nucleic acid sequence. In one aspect of the invention, an amplification site is removed from the oligonucleotide after amplification. In another aspect of the invention, an amplification site includes one or more restriction endonuclease recognition sequences recognized by one or more restriction enzymes. In another aspect, an amplification site is heat labile and/or photo labile and is cleavable by heat or light, respectively. In yet another aspect, an amplification site is a ribonucleic acid sequence cleavable by RNase. In still another aspect, an amplification site is chemically cleavable (e.g., using acid and/or base).

As used herein, the term "restriction endonuclease recognition site" is intended to include, but is not limited to, a particular nucleic acid sequence to which one or more restriction enzymes bind, resulting in cleavage of a DNA molecule either at the restriction endonuclease recognition sequence itself, or at a sequence distal to the restriction endonuclease recognition sequence. Restriction enzymes include, but are not limited to, type I enzymes, type II enzymes, type HS enzymes, type III enzymes and type IV enzymes. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2005) *Nucl. Acids Res.* 33:D230, incorporated herein by reference in its entirety for all purposes).

In certain aspects, primers of the present invention include one or more restriction endonuclease recognition sites that enable type HS enzymes to cleave the nucleic acid several base pairs 3' to the restriction endonuclease recognition sequence. As used herein, the term "type HS" refers to a restriction enzyme that cuts at a site remote from its recognition sequence. Type HS enzymes are known to cut at a distances from their recognition sites ranging from 0 to 20 base pairs. Examples of Type Hs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-Hs endonucleases are commercially available and are well known in the art (New England Biolabs, Ipswich, Mass.). Information about the recognition sites, cut sites and conditions for digestion using type Hs endonucleases may be found, for example, on the Worldwide Web at neb.com/nebecomm/enzymefindersearch bytypells.asp). Restriction endonuclease sequences and restriction enzymes are well known in the art and restriction enzymes are commercially available (New England Biolabs).

Certain exemplary embodiments are directed to the use of computer software to automate design and/or interpretation of genomic spacings, repeat-discriminating SNPs and/or colors for each specific oligopaint set. Such software may be used in conjunction with individuals performing interpretation by hand or in a semi-automated fashion or combined with an automated system. In at least some embodiments, the design and/or interpretation software is implemented in a program written in the JAVA programming language. The program may be compiled into an executable that may then be run from a command prompt in the WINDOWS XP operating system. Unless specifically set forth in the claims, the invention is not limited to implementation using a specific programming language, operating system environment or hardware platform.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables, and accompanying claims.

Example I

Overall Strategy for Oligopaint Design

1. Give centromeres an identifying color: e.g., can either make all centromeres the same color, or make chromosome-specific.
2. Query whether minor M-bands will obscure major M-bands. Minor: major M-band ratios such as, e.g., 1:1, 2, 3, 4, 5, 10, 20, 50, 100 will be tried.
3. Query what distance the M-bands should be from one another to be distinct. 250 and 500 kb, as well as 1, 2, 3, 4, 5, 6, 7, 8, 9, and 10 Mb will be tried.
4. Whether there is a pattern of I- and M-bands (varying color, thickness) that can uniquely identify regions will be determined. All combinations of 2, 3, 4, & 5 colors, spaced 50, 100, 200, 500, and 750 kb, and 1 and 2 Mb apart for separation and color interference will be tested. Five colors in a never-repeating pattern may permit unambiguous tagging of all genomic regions, but may raise challenges: a) condensation, which can also be uneven, may change colors. Varying band widths of a color may avoid issues because (without intending to be bound by scientific theory) condensation should not change hue.
5. How close (far apart) I-bands must be to make a single band (be distinct) will be determined. Try 10, 30, 50, 75, 100, 150, 200, 500, 750, and 1000 kb.
6. How many x-mers are needed to produce an I-band will be determined. A contiguous 1, 3, 5, 7, and 10 kb will be labelled for all colors.
7. How long the probe/primer sequences should be will be determined. Probe lengths of 40-28 bases and corresponding primer lengths of 10-16 bases will be tested, and this will be done for varying GC content. Pre-selections will be performed to avoid overlap with other primers and any unique sequence in the genome. Also, primers can be extended by adding tails after synthesis of array. Primers and extensions will be designed such that they do not overlap unique sequence other primers.
8. Watson & Crick strands will be separately labelled. Different primers will be used for 5' and 3' ends, and N will be placed on only one of the two.
9. Whether universal primers should be used will be determined. Although universal primers can be used, although their usefulness is unclear.
10. Targets will be pre-selected to minimize partial homology to repetitive elements to avoid repetitive sequences. If problems arise after arrays are made, the following steps may be employed: a) compete with unlabeled probe, b) remove oligo from library by hybridizing w/i) homologous RNA and removing by anti-RNA/DNA or ii) homologous DNA-biotin, putting through column.
11. Other avenues: a) Electron dense material will be used for EM studies, b) bleeding of colors will be used to help study condensation.
12. Give unique colors to: ultraconserved elements (UCEs) (e.g., intergenic/introic/exonic); imprinted regions; allelically skewed genes; exons; cell-type (e.g., stem) markers and the like.

Example II

Restriction-Free Protocol to Make Oligopaint Probes

Figure 5:
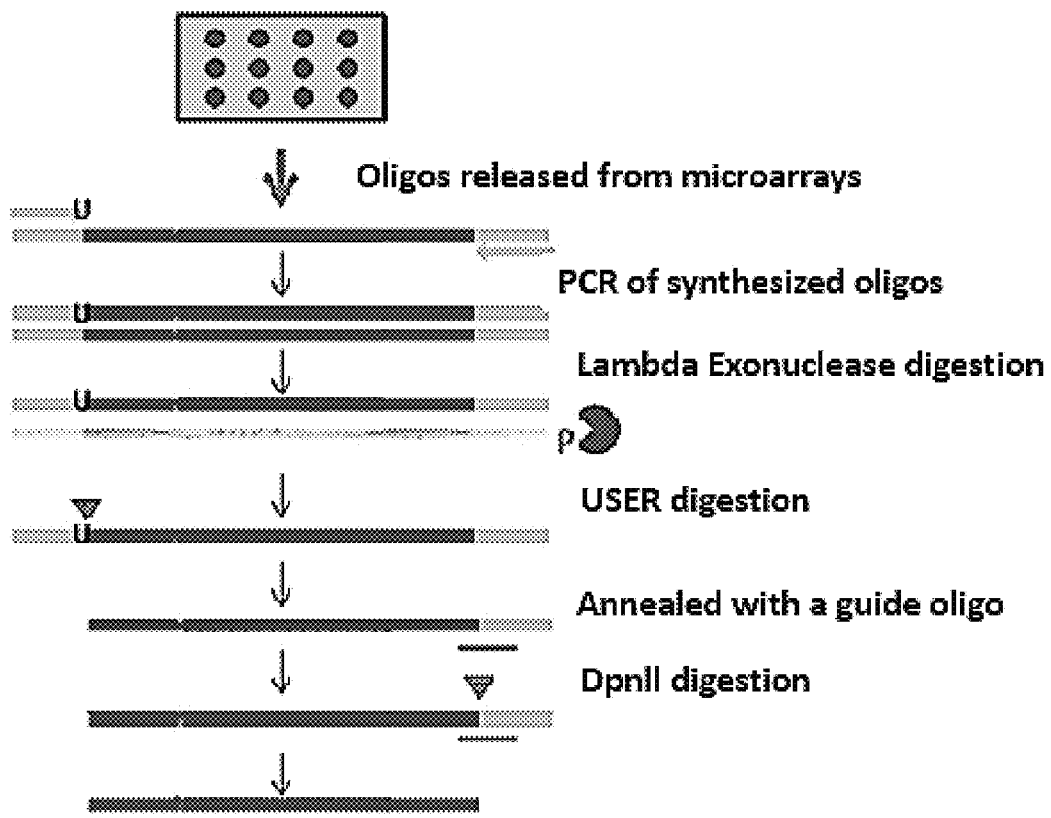
FIG. 5 schematically depicts one protocol to make Oligopaint probes from chip-synthesized oligonucleotide libraries.

The basic idea is to make 60-mers on the Agilent platform: 10 base on each end for the quasi-universal primers and 40 bases in the middle representing the unique regions of the human genome (FIG. 5).

Parameters:
1. Minimum density 40-mer tiling (half that, ¼, ⅛, etc.)
2. Minimum length: 5 kb (3 kb, 7 kb, 9 kb)
3. Minimum interphase distance between bands: 40 kb (20, 60, 80)
4. Minimum metaphase distance between bands: 4 Mb (2, 6, 8)
5. Length of primers: 10 bp (9, 12, 14, 15)

Given a 40:1 compaction ratio for 30 nm chromatin, the DNA:Interphase(I):Metaphase(M) compaction ratios for chromosome 19 are (64 Mb) 21 mm:500 microns:5 microns=4000:100:1. A microscopic resolution of 300 nm means 40 kbp/pixel interphase and 4 Mbp/pixel for metaphase.

Goals for Color Layout:
1) Know the location in I or M with minimal context and counting.
2) Be suitable for human or computer reading
3) Have one set of paints to cover the interphase to metaphase transition
4) Be able to uniformly label by whole chromosome or by arm or by strand.
5) Be able to selectively amplify from up to 100 chips which don't necessarily neatly end at the arm boundaries.

Assuming that 5 kb of solid (unique) 40-mers is enough to detect as a band in both I & M, 35 kb between bands in I, 4 Mb in M. Human chromosomes range from 47 Mb=16 M-bands (#21) to 247 Mb=80 bands (#1).

Each set of 4 M-bands is enough to encode 5^4=625 bands (enough to cover the 800 such overlapping 16 Mbp regions with some redundancy considering that the I-bands contribute a 5th). Each M-band has 100 I-bands. Ten I-bands are enough to encode a unique (7 bit, $2^1\backslash7=128$) binary pattern, which can be augmented with 3 check bits and repeated 10 times, for example:

Chromosome 1=4 sets of 4 M-bands—with I-band color in parenthesis, 50 to 90 bands out of 100 (v. 1 out of 100 for M-bands): 4(5 . . . )4(5 . . . )4(5 . . . )4(5 . . . )1(5 . . . ) 4(5 . . . )4(5 . . . )4(5 . . . )2 (see scenario #1 below).

Expanding the first of the 16 M-bands below:

| Paint: | 45555.55.5.5555.55.5.5555.55.5.5555.55.5.5555.55.5 | .5555.55.5.45 |
|---|---|---|
| 1s digit | 0123456789012345678901234567890123456789 | 0123456789012 |
| 10s digit | 0000000000111111111122222222223333333333 4444444444 . . . | 9999999999000 |
| 100s digit | (Position 0 to 102) | 111 |

A De Bruijn sequence B(k, n) is a cyclic sequence of a given alphabet size k for which every possible subsequence of length n appears as a sequence of consecutive characters exactly once (length=k^n) (See Worldwide Website hakank org/comb/deBruijn.Applet.html).

Scenario #1: Chips are generated in order of position on the genome, so by labeling one chip out of N, that fraction of the genome is obtained (this is not going to perfectly coincide with a chromosome boundary unless a few chips are wasted). Below are five B(4,4) sequences (5*256 M-bands each) which should be more than enough for encoding the roughly 800 M-bands (depending on optimal density from the first chip experiment). In each set below the (missing) 5th color is the (dominant) I-band color. In this case each color has its own primer pair (5 total). Note that since these sequences are 256 characters long, they don't fit on the line but instead wrap to the next line. The first 256-mer below assumes an I-band color #5:

44441444244434411441244134421442244234431 4432
44334141424143411141124 1134
12141224123413141324133424243421142124 21342
214222422342314232423343 43114
31243134321432243234331433243 331111211131122
1123113211331212131 222122312
3212331313221323133213332222322332 323333
555515552555355115512551355215522552355315 532
55335151525153511115112511 35

121512251235131513251335252535211521252 13522
15222522352315232523353 53115
312531353215322532353331533253333111 1211131122
112311321133121213122 2123 12
321233131322132313321333222322332 3233 33
4444144424445441144124415442144224254451 4452
44554141424145411141124 1154
121412241254151415241554242454211421242 15422
142224225425142524255454 5114
51245154521452245254551455245551111211 151122
1125115211551212151222 122512
52125515152215251552155522225225525 25555
44441444544434411441544134451445544534 4314435
44334141454143411141154 1134
151415541534131413541334545434511451545 13455
14555455345314535453343 43114
315431343514354353433143354333111151113 1155
115311351133151513155515 5315
35153313135513531335133355553553353 53333
4444244454443442244254423445244554453443 24435
44334242454243422242254 2234
252425542534232423542334545434524525452 3455
24555455345324535453343 43224
325453343524355435343324335433332225222 3225
52253223522332525232555 255325
35253323235523532335233355553553353533 33

Scenario #2: As per Scenario #1 except 24 I-band colors (A-X) are used, which means that the De Bruijn alphabet (for the M-bands) can only be k=3 (not 4 colors in Scenario #1) since now two colors are used just for the I-bands. Below are 24 B(3,4) sequences (24*81 M-bands each) which should be more than enough for encoding the roughly 800 M-bands (depending on optimal density from the first chip experiment). In each set below the (missing) 1 or 2 colors combine to form the (dominant) I-band color (or 24 combinations total). Since each I-band has its one primer pair and the five primary colors have their own primer pairs (for the M-bands), in principle anyone could get any combination of chromosome and color combination and strand simply by how the primers are labeled (and independent of chip#). This can be easily extended to all 48 arms by assigning two primer pairs for each of the 24 color-combinations (one each for p & q arms). Since these sequences are 27 characters long, they don't fit on the line and instead wrap to the next line. The first 27-mer below assumes an I-band color using #4 and 5 or just #4 or just #5.

I:4&5: 3 3 3 3 1 3 3 3 2 3 3 1 1 3 3 1 2 3 3 2 1 3 3 2 2
3 1 3 1 3 2 3 1 1 1 3 1 1 2 3 1 2 1 3 1 2 2 3 2 3 2 1 1 3 2
1 2 3 2 2 1 3 2 2 2 1 1 1 1 2 1 1 2 2 1 2 1 2 2 2 2

I:3&5: 4 4 4 4 1 4 4 4 2 4 4 1 1 4 4 1 2 4 4 2 1 4 4 2 2
4 1 4 1 4 2 4 1 1 1 4 1 1 2 4 1 2 1 4 1 2 2 4 2 4 2 1 1 4 2
1 2 4 2 2 1 4 2 2 2 1 1 1 1 2 1 1 2 2 1 2 1 2 2 2 2

I:3&4: 5 5 5 5 1 5 5 5 2 5 5 1 1 5 5 1 2 5 5 2 1 5 5 2 2
5 1 5 1 5 2 5 1 1 1 5 1 1 2 5 1 2 1 5 1 2 2 5 2 5 2 1 1 5 2
1 2 5 2 2 1 5 2 2 2 1 1 1 1 2 1 1 2 2 1 2 1 2 2 2 2

I:2&5: 4 4 4 4 1 4 4 4 3 4 4 1 1 4 4 1 3 4 4 3 1 4 4 3 3
4 1 4 1 4 3 4 1 1 1 4 1 1 3 4 1 3 1 4 1 3 3 4 3 4 3 1 1 4 3
1 3 4 3 3 1 4 3 3 3 1 1 1 1 3 1 1 3 3 1 3 1 3 3 3 3

I:1&5: 4 4 4 4 2 4 4 4 3 4 4 2 2 4 4 2 3 4 4 3 2 4 4 3 3
4 2 4 2 4 3 4 2 2 2 4 2 2 3 4 2 3 2 4 2 3 3 4 3 4 3 2 2 4 3
2 3 4 3 3 2 4 3 3 3 2 2 2 2 3 2 2 3 3 2 3 2 3 3 3 3

I:1&4: 2 2 2 2 5 2 2 2 3 2 2 5 5 2 2 5 3 2 2 3 5 2 2 3 3 2 5 2 5 2 3 2 5 5 5 2 5 5 3 2 5 3 5 2 5 3 3 2 3 2 3 5 5 2 3 5 3 2 3 3 5 2 3 3 3 5 5 5 5 3 5 5 3 3 5 3 5 3 3 3 3

I:1&3: 2 2 2 2 5 2 2 2 4 2 2 5 5 2 2 5 4 2 2 4 5 2 2 4 4 2 5 2 5 2 4 2 5 5 5 2 5 5 4 2 5 4 2 5 4 4 2 4 2 4 5 5 2 4 5 4 2 4 4 5 2 4 4 4 5 5 5 5 4 5 5 4 4 5 4 5 4 4 4 4

I:1&2: 4 4 4 4 5 4 4 4 3 4 4 5 5 4 4 5 3 4 4 3 5 4 4 3 3 4 5 4 5 4 3 4 5 5 5 4 5 5 3 4 5 3 4 5 3 3 4 3 4 3 5 5 4 3 5 3 4 3 3 5 4 3 3 3 5 5 5 5 3 5 5 3 3 5 3 5 3 3 3 3

I:2&3: 4 4 4 4 5 4 4 4 1 4 4 5 5 4 4 5 1 4 4 1 5 4 4 1 1 4 5 4 5 4 1 4 5 5 5 4 5 5 1 4 5 1 4 5 1 1 4 1 4 1 5 5 4 1 5 1 4 1 1 5 4 1 1 1 5 5 5 5 1 5 5 1 1 5 1 5 1 1 1 1

I:2&4: 1 1 1 1 5 1 1 1 3 1 1 5 5 1 1 5 3 1 1 3 5 1 1 3 3 1 5 1 5 1 3 1 5 5 5 1 5 5 3 1 5 3 1 5 3 3 1 3 1 3 5 5 1 3 5 3 1 3 3 5 1 3 3 3 5 5 5 5 3 5 5 3 3 5 3 5 3 3 3 3

TABLE 1

| Chromosome# | Mb |
|---|---|
| 1 | 447 |
| 4 | 444 |
| 4 | 400 |
| 4 | 191 |
| 5 | 181 |
| 6 | 171 |
| 7 | 159 |
| 8 | 146 |
| 9 | 140 |
| 10 | 145 |
| 11 | 144 |
| 14 | 144 |
| 14 | 114 |
| 14 | 106 |
| 15 | 100 |
| 16 | 89 |
| 17 | 79 |
| 18 | 76 |
| 19 | 64 |
| 40 | 64 |
| 41 | 47 |
| 44 | 50 |
| 44-X | 155 |
| 44-Y | 58 |
| | 4079 |

REFERENCES

Schrock et al. (1996) *Science* 474(5474):494
Worldwide Website: ncbi.nlm.nih.gov/pubmed/11044455
Worldwide Website: ncbi.nlm.nih.gov/pubmed/10479870
Worldwide Website: ncbi.nlm.nih.gov/pubmed/8664547
Cross-species color segmenting or RxFISH, barcodes from fragmented hybrids (Worldwide Website: chrombios.com/AboutFISH/BarCodes.html)
Multicolour (44 color) fluorescence in situ hybridisation (mFISH), multicolour banding analysis (mBAND), region-specific partial chromosome paints from Metasystems (Germany) (Worldwide Website: ori.nus.edu.es/MCytogenetics.html)
Multicolor FICTION, DNA labelling were diethylaminocoumarin (DEAC), SpectrumGreen™ (SG), SpectrumOrange™ (SO), Texas Red® (TR) and Cyanine 5 (Cy™5), detection of the immunophenotype was performed with aminomethylcoumarin (AMCA) (Worldwide Website: metasystems.de/customers/a04/a04.htm)
All STAR*FISH paint systems for whole human chromosomes (Worldwide Website: openbiosystems.com/FISH-probes/Starfish/Human/Multicolor/)
CTs 4 green (labeled with dinitrophenol, detected with FITC), CTs 5 blue (labeled with digoxigenin, detected with Cy4), and CTs 11 red (labeled with biotin, detected with Cy5) (Worldwide Website: cshprotocols.cshlp.org/cgi/content/full/4007/10/pdb.prot4740/F4).

Example III

Making Probes Using dU Digestion

To determine whether USER™-digested, synthesized oligonucleotides having an internal fluor could be used in FISH, 60 base pair probes were synthesized (as versus PCR amplified), mimicking what would be expected if the oligonucleotides had been generated by PCR. The probes contained 32 base pairs of homology to a locus in *Drosophila* that contains approximately 110 copies of the target sequence. Both strands of a 60 base pair oligonucleotide having internal dUs and internal fluors were synthesized. The two synthesized oligonucleotides were mixed in equal portions and cleaved at the dUs with the USER™ (uracil-specific excision reagent) enzyme (New England Biolabs, Ipswich, Mass.). The oligonucleotides were then used for FISH, with a single-stranded 32 base pair oligonucleotide targeting a different sequence in the same region as a control.

Figure 7:
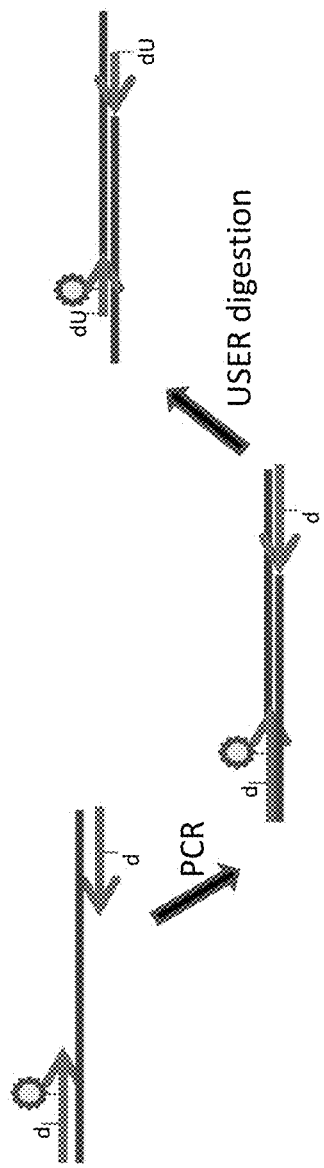
FIG. 7 schematically depicts the use of PCR primers that include an internal dU and an internal fluor, enabling digestion of the 5' end of the primers with USER™ (uracil-specific excision reagent) (New England Biolabs, Ipswich, Mass.).

It was determined that double stranded, 32 base pair oligonucleotides could be used as FISH probes, but double stranded, 60 base pair oligonucleotides could not. Since the double stranded PCR products would be 60 base pairs in length, a strategy was developed for modifying them prior to FISH. PCR primers that carried an internal dU and an internal fluor were used such that the 5' ends of the primers could be excised with USER™ subsequent to PCR (FIG. 7). It was determined that USER™-digested, synthesized (not PCR amplified) oligonucleotides could be used in FISH.

Having determined that the use of internal dUs and internal fluors permitted synthesized, double stranded, 60 base pair oligonucleotides to be used as probes, it was next queried whether analogous PCR generated 60 base pair oligonucleotides could also be used as probes. It was determined that USER™-digested, PCR generated, double stranded, 60 base pair oligonucleotides could indeed be used in FISH.

Synthesized Oligonucleotides

USER™-digested, synthesized oligonucleotides were used in FISH at 100 ng, 200 ng, 400 ng and 800 ng concentrations. 200 ng of single stranded, 32 base pair oligonucleotide was used as a control. FISH was performed as follows: 30 minute hybridization at room temperature, two 10 minute washes, auto leveled using Photoshop, 60× objective, NA=1.2, 1 second exposure.

PCR Generated Oligonucleotides

USER™-digested, PCR generated oligonucleotides were used in FISH at 50 ng, 100 ng, 200 ng and 400 ng concentrations. 200 ng of single stranded, 32 base pair oligonucleotide was used as a control. FISH was performed as follows: 30 minute hybridization at room temperature, two 10 minute washes, auto leveled using Photoshop, 60× objective, NA=1.2, 1 second exposure.

Example IV

Enhancing Signal to Noise

Many protocols relying on hybridization of nucleic acid probes to nucleic acid targets aim to optimize signal to noise by increasing the affinity of the probe to its target and decreasing the affinity of the probe to background. The following strategies will be used to increase signal to noise ratios:

1. The length of the probe will be extended via polymerization along a nucleic acid target, e.g., a chromosome, thereby increasing the affinity of the probe to its target. Without intending to be bound by scientific theory, probes that are incorrectly hybridized to targets or non-specifically bound to non-nucleic acid substrates will not be subject to extension, thus increasing signal to noise ratios.

2. Probes that include one or more quenchers and one or more fluorescent tags will be used such that when a probe is hybridized to a nucleic acid target and extended, the quenchers will be released. Without intending to be bound by scientific theory, this should enhance signal to noise ratios.

3. When hybridizing probes to cells or other complex targets, the amount of non-nucleic acid substrates present will be reduced through the use of proteinases, lipases and the like. Without intending to be bound by scientific theory, this should enhance signal to noise ratios.

Example V

Oligopaints

Currently, companies such Open BioSystems and Metasystems use FACS-sorted chromosomes, which can also be microdissected into smaller fragments, to generate chromosome paints. This approach can provide up to 500 colored bands of per haploid genome (Metasystems), corresponding to approximately 6 Mb of DNA per band. The price of these paints ranges from approximately $100 to $4,000 per genome per assay, with chromosome paints that provide higher resolution costing significantly more than whole chromosome paints.

Figure 2:
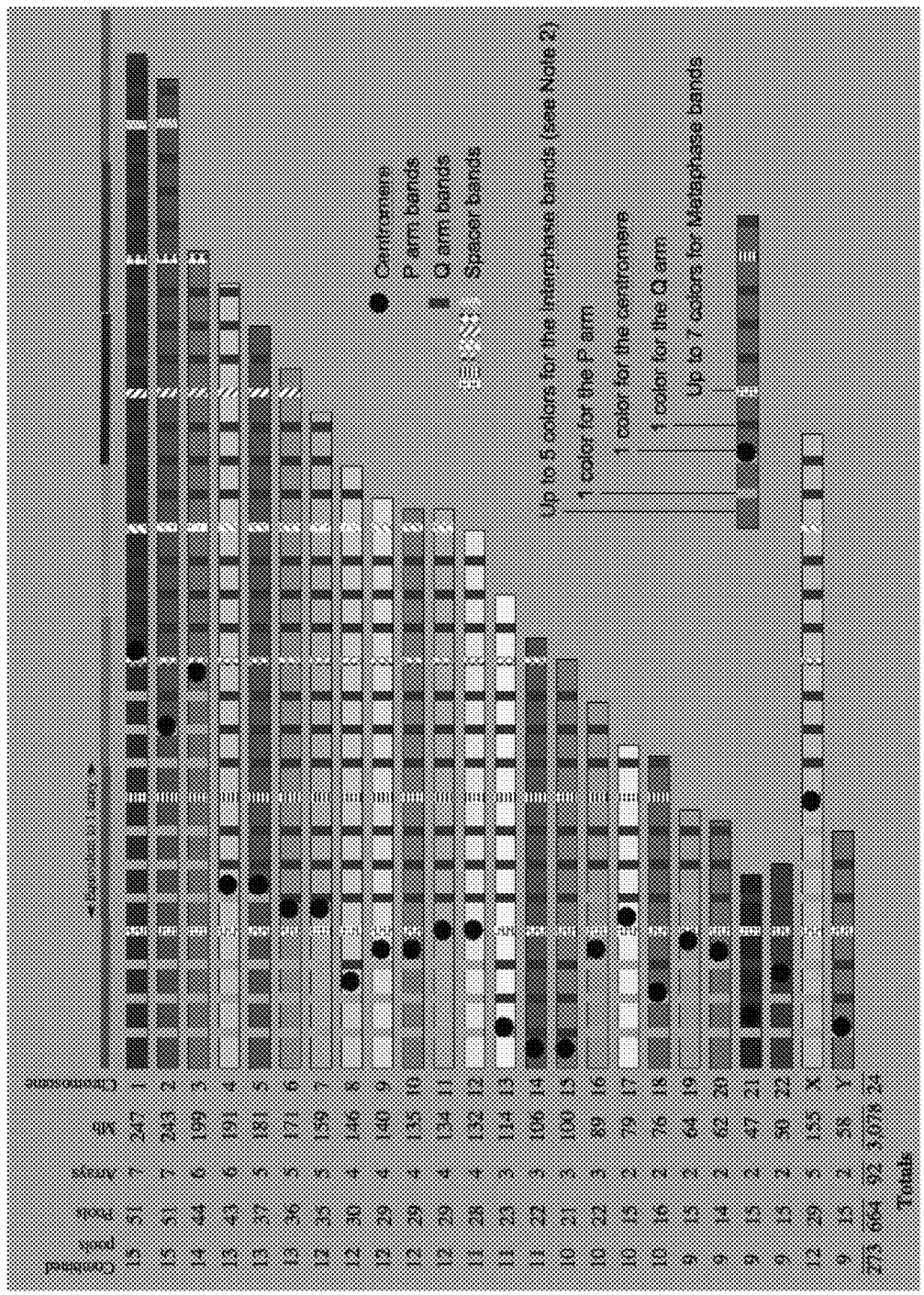
FIG. 2 schematically depicts one method of making 20% of the human genome on up to 92 arrays which, after amplification with between 5 and 15 (=5+1+1+1+7) different kinds of primer pairs, will generate 664 pools of genomic sequence. The pools can be combined in a variety of ways to target chromosomes or sub-chromosomal regions.
Figure 3:
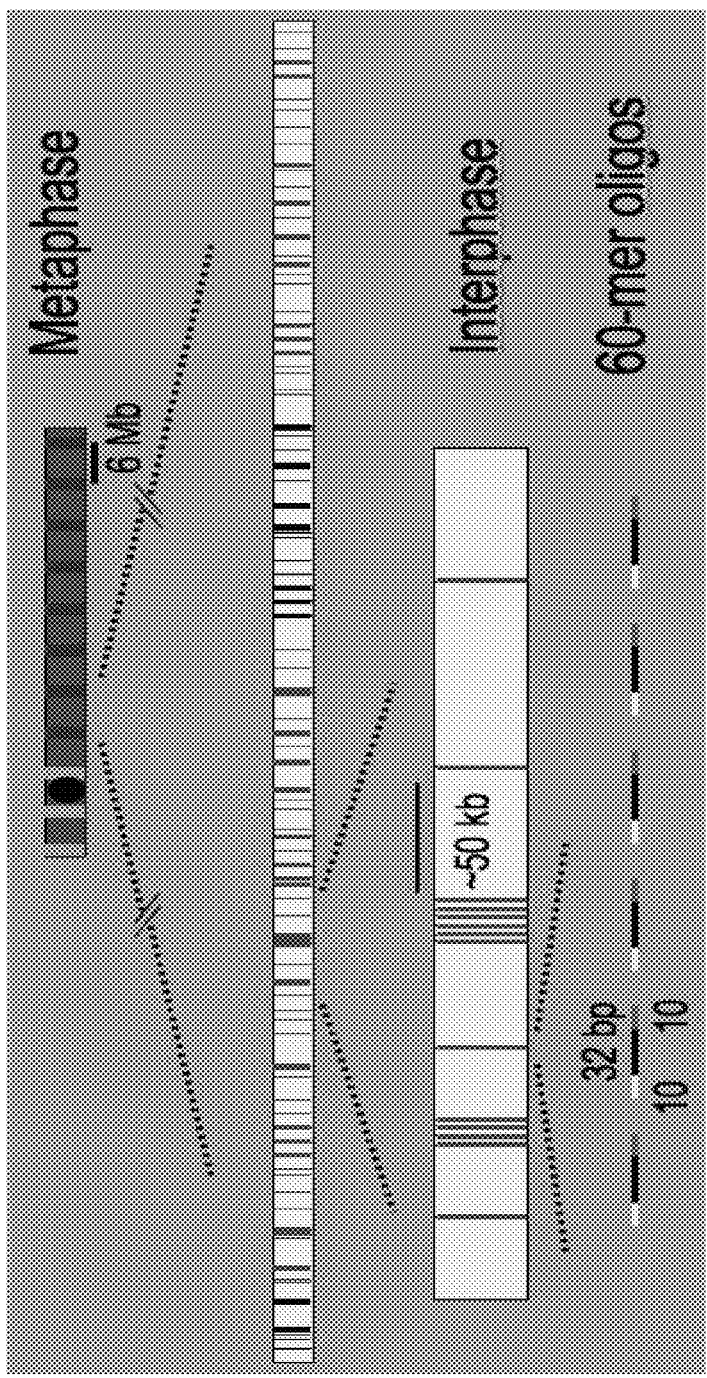
FIG. 3 schematically depicts how thick banding will become a finer pattern on decondensed chromosomes.
Figure 4:
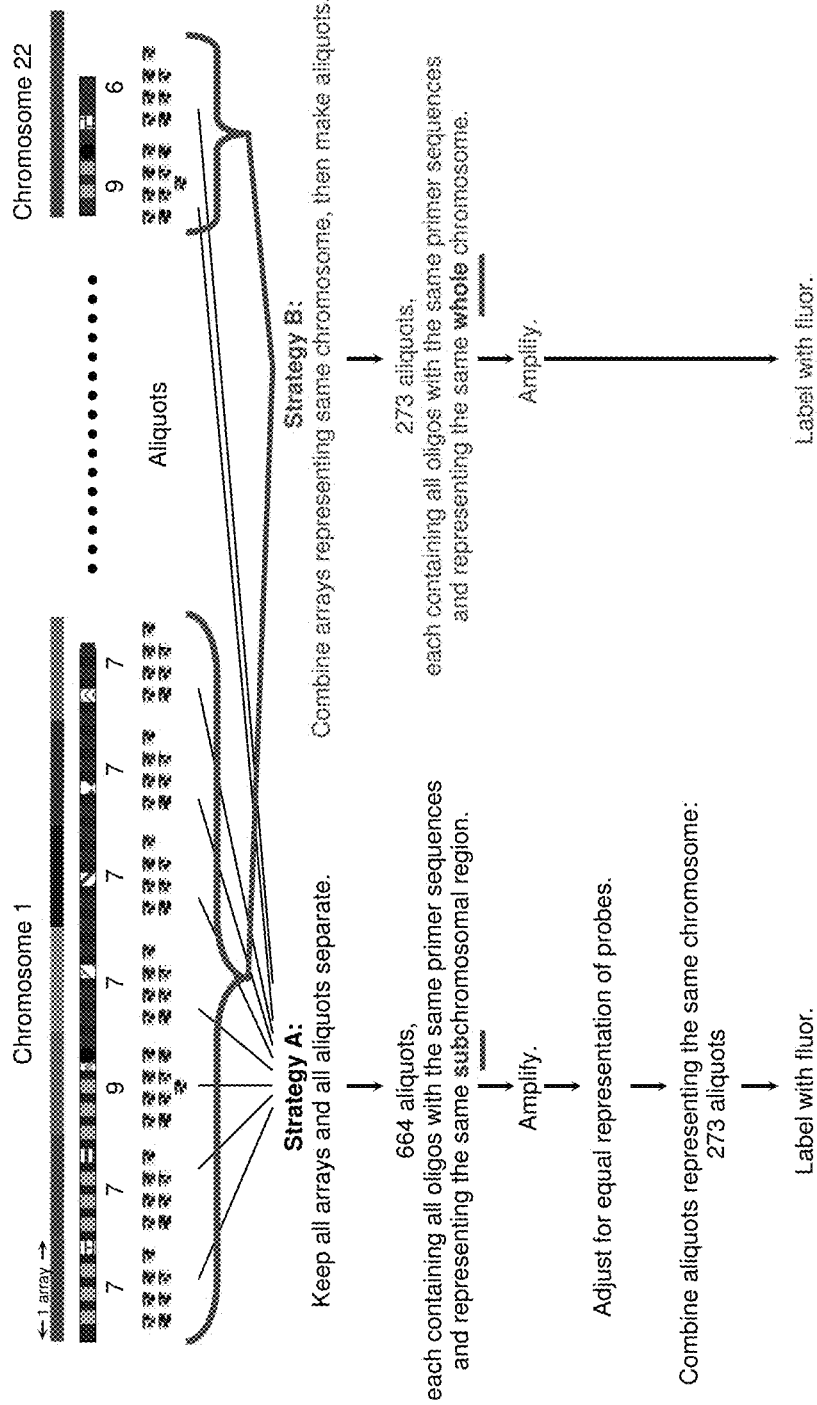
FIG. 4 schematically depicts strategies for aliquoting. Either strategy allows for the visualization of just one or a few chromosomes at a time, as well as permitting the visualization of sub-chromosomal regions. Aliquots carrying different primer sequences can be labeled with the same marker if there is no need to distinguish the targets by fluorescent in situ hybridization (FISH).

The cost of paints can be greatly reduced by synthesizing them via PCR amplification of oligomers (e.g., 60-mers) that consist of genomic sequences (e.g., 32-mers) (representing only the unique part of the genome) flanked by primer sequences (e.g., 14-mers) and, in total, represent 20% (although the oligomer lengths and percentages may differ depending on array optimization experiments, the type of genome, the AT content of the genome, spacing of repeated sequences with unique sequences, etc.) of the human genome (FIG. 1). Oligomer sizes described in this paragraph (e.g., primer sequences and/or genomic sequence) may be increased or decreased based on the results of optimization experiments. These 60-mers will be synthesized on Agilent 244K arrays at the cost of $500 per array such that 20% of the human genome will be contained on 80 to 95 arrays (FIG. 2). Judicious design and use of the primer sequences will then, in conjunction with the subdivision of the genome into 80 to 92 sub-chromosomal arrays, allow for the separate amplification and labeling of approximately 664 pools of genomic sequence. Application of all 664 pools of probe will then constitute a whole genome chromosome paint which, without intending to be bound by scientific theory, will produce a crisp banding pattern on metaphase chromosomes and increasingly finer banding patterns on increasingly decondensed chromosomes (FIG. 3). Importantly, after the initial expense of the arrays, the cost of maintaining the templates by PCR for the future batches of paints will be minimal, dropping the cost of the paints to dollars per assay (including the cost of primers and dyes). Each step of this protocol has been carried out successfully.

The Oligopaints and methods of making them described herein provide numerous advantages over chromosome paints that are commercially available. For example, Oligopaints and methods of making them provide: 1) increased resolution over chromosome paints that are commercially available; 2) reduced price over chromosome paints that are commercially available; 3) availability for any organism for which there is a genome sequence, even if that sequence is partial (that is, YACs, BACs and/or chromosomes that are sortable (e.g., by FACS) are not necessary); 4) the ability to avoid background issues caused by repetitive sequences, because the use of repetitive sequences can be avoided (in contrast, chromosome paints that are commercially available use "cold" (i.e., unlabeled) repeat sequences to outcompete the labeled probes; 5) the option to eliminate certain bandings by not amplifying probes to those bands (e.g., after an array has been generated); 6) the option to redesign arrays to fit individual needs; and 7) the ability to specifically label certain sequences by giving them identifying primer sequences.

The Oligopaints described herein are useful for a variety of methods including, but not limited to: 1) heterologous and/or homologous (e.g., pairing) interchromosomal interaction studies; 2) intrachromosomal organizational studies such as, e.g., looping, coiling and the like; 3) chromosome organizational studies, such as, e.g., chromosome path, placement of specific sequences and the like; 4) chromosome condensation studies, such as, e.g., mitosis, meiosis, arrest during cell cycle and the like (new colors will be generated when Oligopainted bands overlap and/or 'bleed' into one another); 5) chromosome behavior studies such as, e.g., segregation, motion in non-dividing cells and the like; 6) karyotyping studies such as, e.g., for medical science (e.g., diagnostic karyotyping, amniocentesis, pre-implantation diagnosis and the like), for basic science, to detect copy number variations (CNVs) and other chromosomal rearrangements, changes in ploidy and the like; 7) replication studies such as, e.g., timing, organization, Bell nuclei and the like; 8) chromosome structure studies such as, e.g., organization at the electron microscopy level and the like; and 9) strand specific biology of DNA through separate labeling of each of the two strands of a DNA double helix).

FIG. 1 illustrates how a new form of chromosome paints, Oligopaints, can be made from template oligonucleotides which are synthesized on arrays (e.g., chips). Primers are annealed to sequences on the array and then extended to generate a 60-mer products which could then be dissociated from the array and used for second strand synthesis. Products are then aliquoted into smaller pools which could be amplified with a single primer pair each. Finally, chromosome paints are made by amplifying the pools with primers containing two or more dU nucleotides and a fluorescent dye at the 3' end, followed by cleavage at the dUs to reduce inter-primer annealing. Note that if the two members of a primer pair are different in sequence, it will be possible to differentially label the two strands of DNA, enabling strand-specific hybridization to DNA or RNA. Note that the first few steps could be simplified if the original synthesized oligonucleotide can be released from the array. In certain exemplary embodiments, the use of dU allows for cleavage of primer sequences (at the dU), which will reduce the concentration of primer sequences present during hybridization.

FIG. 2 schematically depicts how the 24 chromosomes of the human genome could be differentially colored with a base color for the interphase bands being a mix of five primary colors, and a series of color-coded metaphase bands at staggered positions along the p and q arms. These patterns will be generated by computer algorithms that select unique sequences along the chromosomes and then associate them with primer sequences such that their amplification with corresponding oligos carrying the correct balance of dyes, followed by hybridization to the chromosome, which, without intending to be bound by scientific theory, will likely create identifying banding patterns for sub-chromosomal regions, especially when the chromosome is decondensed.

FIG. 1 shows how a band that appears thick on a metaphase chromosome will likely disperse into a pattern of thinner bands, which it is hoped will demarcate specific chromosomal regions on the order of 10-50 kb in size. Currently, arrays are being synthesized to a) confirm preliminary data demonstrating that 14 base pair primers are sufficiently robust for use in PCR amplification, b) determine how many oligonucleotide probes are necessary to generate a visible band in interphase and/or metaphase, c) determine how far apart oligonucleotide probes must be to generate distinct bands in interphase and/or metaphase, d) assess what level of variation there may be in banding patterns from one chromosomal region to another, e) determine what level of interference there may be when fluorescent dyes are tightly packed, and f) ascertain whether the interference can be taken advantage of to assess degrees of chromosome condensation. Analogous arrays for the *Drosophila* and *C. elegans* genomes are also being designed for ongoing projects studying pairing in these organisms.

One innovative aspect of the oligopainting methods and compositions described herein is the use of computationally patterned synthetic probes and arrays (rather than natural DNAs/chromosomes) to generate chromosome paints. This strategy will enable huge improvements in cost and resolution.

Example VI

Homology Effects

Oligopaint technology will enable the systematic investigation of tumor cells and cancer cell lines in terms of their chromosome arrangement and positioning and, in doing so, will both emphasize experiments that are often not routinely considered in terms of cancer as well as demonstrate an affordable resource that will make such experiments generally feasible. Oligopaint technology will also enable the search for genes involved in somatic homolog pairing by permitting whole genome FISH-based screens of the human genome using Oligopaints in the format of 384-well plates. It was determined that FISH-based screens in 384-well plates was successful. However, many in the art have predicted that such an approach would not be technically and/or practically feasible for whole genome screens, especially if the FISH were to target unique sequences. Oligopaints will make this approach both technically and practically feasible. As a whole-genome Oligopaint FISH-based strategy offers a new for approach for identifying genes that affect chromosome organization, it will open up new lines of investigation. In particular, attempts will be made to identify genes that promote homolog pairing, as such genes could be used to enhance gene replacement and gene therapy strategies that rely on homologous recombination.

Human chromosome karyotyping is a routine procedure for the analysis of cancer genotypes as well as many genetic diseases, such those associated with a multitude of birth defects associated with whole chromosome anueploidies, deletions, duplications, translocations and inversions. Furthermore, with the increased awareness of copy number variation and the association of such chromosomal structures with disease, the demand for karyotyping grows along with the need for increased accuracy.

Chromosome painting improves the power of karyotyping by color-coding chromosomes and sub-chromosomal segments. The ability of physicians to visualize the underlying chromosomal basis for disease is key for accurate diagnosis and treatment, making the availability of affordable painting techniques a top priority in the medical innovation.

Better painting technologies will also impact the fields of genetic counseling and prenatal diagnosis. Here, the accuracy of karyotyping is frequently the determining factor in the quality of information physicians and genetics counselors can offer patient clients seeking explanations for their ailments or wishing for a deeper understanding of the genotypes they have inherited and may pass on to their children. Unlike the karyotyping of patients whose disease syndromes will often have already suggested likely chromosomal abnormalities, clients seeking genetic counseling or prenatal diagnoses often seek information without any underlying syndromes. In these situations, the accuracy of the analyses will rest to a great extent on the resolution of chromosome paints across the entire genome and, therefore, the higher the resolution of the paints, the more reliable will be the information obtained. Unfortunately, high resolution paints can cost thousands of dollars for a single assay of an entire human genome. One goal is to produce chromosome paints of the highest resolution for a fraction of the cost of current high resolution paints. As such, resources will be available to all populations, especially those for whom medical services are already an excessive financial burden.

Finally, the methods and compositions described in herein should affect a broad spectrum of research fields, including those focusing on chromosome organization, chromatin structure, interchromosomal interactions, chromosome transmission, homology effects, replication, homologous recombination, genome integrity, and genome evolution. These fields center to a great extent on the concept of the chromosome as an entity in and of itself, something more than a repository of genes. As chromosomes are difficult to study in their entirety except when examined in situ, protocols for visualizing them are of utmost importance.

Using techniques ranging from traditional genetics to FISH, 3C analysis, 4C analysis, 5C analysis and microarrays, researchers are cataloguing hundreds of interchromosomal interactions, some being specific between two loci and others arising from the clustering of loci at transcription factories or other nuclear structures. In short, the popular view of a gene, with enhancers and promoters arrayed along a single black line, has been found lacking. The oligopainting methods and compositions described herein will enable one of skill in the art to focus on homology effects. Homology effects encompass the many forms of gene regulation that are sensitive to, or reflect, the presence of homology within a nucleus. The most celebrated of these would include three processes that occur in humans and other mammals: X-inactivation, where one of two X chromosomes is inactivated (Bacher et al. (2006) *Science* 311:1149; Xu et al (2006) *Science* 311:1149, Epub 2006 Jan. 19)) monoallelism (Borst (2002) *Cell* 109(1):5; Yang et al. (2007) *Cell* 128:777), where only one allele of a gene is expressed, and parental imprinting, a form of monoallelism that reflects the parental origin of each allele (Edwards et al. (2007) *Curr. Opin. Cell Biol.* 19:281; Pauler et al. (2007) *Trends Genet.* 23:284). Homology effects are also abundant in fungi, insects, worms, and plants. For example, a mere 450 base pairs of homology introduced by a transgene into the fungus,

*Neurospora*, will trigger C to T mutations within the duplicated regions (Selker (2004) *Cold Spring Harb. Symp. Quant. Biol.* 69:119), while 90 base pairs of homology between a transgene and the tobacco genome will cause methylation and silencing (Matzke and Matzke (2004) *PLoS Biol.* 2:E133). These phenomena demonstrate an uncanny ability of organisms to respond to homology and, as these responses to homology affect gene regulation, homology effects are of great relevance to human development and health.

Some homology effects are brought about through physical pairing of the interacting homologous genes and/or chromosomal regions. Examples of these types of homology effects are now known to occur in a wide variety of species, including humans and other mammals, insects and fungi.

Among the most dramatic in mammals would be X-inactivation, where pairing of the X-inactivation center plays a role in the counting of X chromosomes and the subsequent process of inactivation. Mammals, like *Neurospora*, also sport a process call meiotic silencing of unpaired DNA/chromatin (MSUD/C) (Turner (2007) *Development* 134:1823), wherein regions of the genome that remain unpaired in meiosis are silenced. Without intending to be bound by scientific theory, this process may explain the curious phenomenon of meiotic sex chromosome silencing, which occurs in male meiosis and targets the unpaired regions of the X and Y chromosomes.

It has been determined that pairing can cause enhancers of a gene to act in trans on the promoter of another gene lying on a separate chromosome, and the cis-trans choice of an enhancer can be controlled by the integrity of the promoter lying in cis to the enhancer. Pairing of an internally deleted gene with a homolog bearing an insulator can lead to changes in gene topology which allow bypass of the insulator (Morris et al. (1998) *Proc. Natl. Acad. Sci. USA* 95:10740). These two mechanisms of pairing-mediated changes in gene regulation argue that somatic homolog pairing is a potent form of gene regulation that warrants analysis in any diploid organism, including humans.

The oligopainting methods and compositions described herein can be used to identify factors that mediate homolog pairing and, to this end, genetic screens have been conducted in *Drosophila*. While such an approach has pointed to a handful of candidate genes involved in gene regulation and chromosome structure (e.g., Hartl et al. (2008) *Science* 322:1384; Williams et al. (2007) *Genetics* 177:31), progress has been slow because past genetic screens have had to rely on observations of pairing-sensitive phenotypes, which are sufficiently removed from the process of pairing that they can complicate analyses. These screens have also been hindered by the need for organismal viability and the multi-tissue nature of the whole organism, which prohibits finer levels of structural analyses. For these reasons, much effort has been exerted to establish a *Drosophila* cell culture system for the analysis of pairing via FISH assays. Cell culture provides homogeneous populations of cells for biochemical and molecular biological analyses (Ashe et al. (1997) *Genes Dev.* 11:2494).

Figure 6:
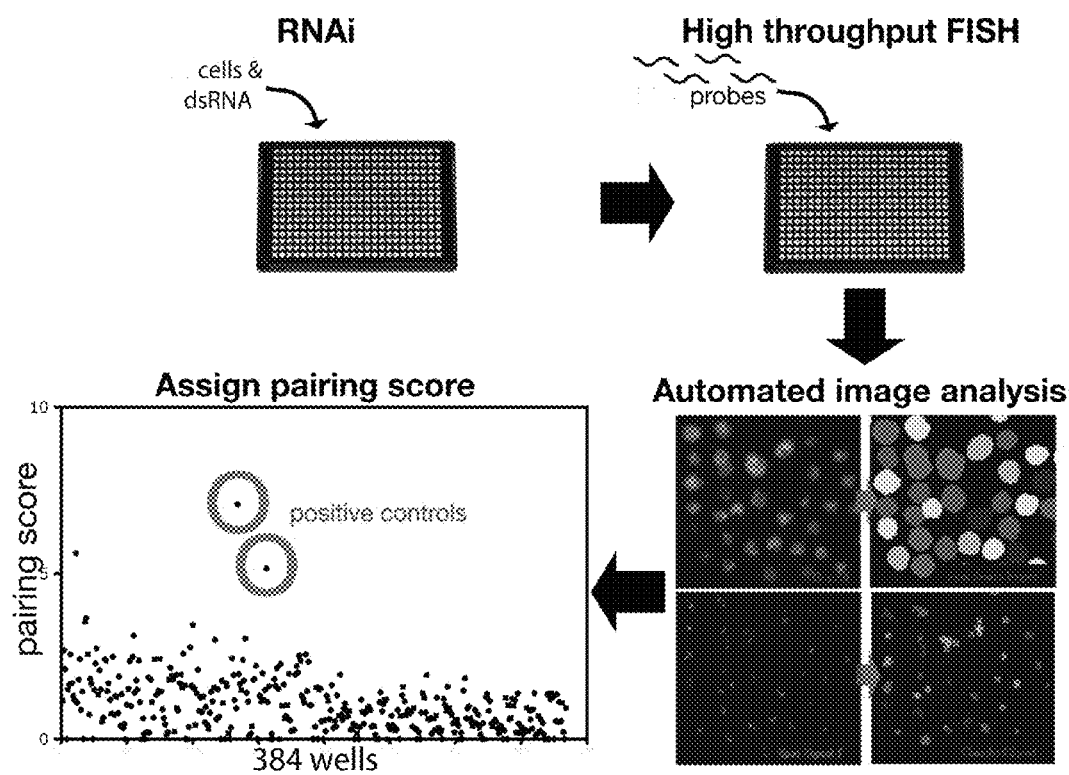
FIG. 6 depicts an RNAi screen for genes involved in *Drosophila* cells, locked nucleic acid (LNA) probes and automated scoring.

A protocol permitting FISH assays in the 384-well format was developed. Using this protocol, sub-genome pilot runs surveyed 11% of the RNAi library representing the *Drosophila* genome, yielding a handful of candidate genes (FIG. 6). These runs addressed two important points. First, they documented the feasibility of FISH in the 384-well format. Second, they demonstrated the capacity of computerized image analysis to detect changes in the pattern of FISH signals from well to well. As discussed further below, this protocol will be adapted for use with human cells.

The biology of pairing will be studied, and studies will begin with a survey of human transformed cells taken directly from a wide variety of tumors as well as cell lines. FISH will be applied using whole genome Oligopaint methods and compounds described herein and to determine the state of pairing along the length of each chromosome arm, taking advantage of computer-based imaging techniques to allow the examination of individual chromosomes or any combination of thereof.

To detect low levels of pairing or pairing that may be specific for certain phases of the cell cycle, at least 100 cells per arm will be scored, and whether the cells appear to be entering mitosis or not will be recorded. Because the degree of proximity may vary along a chromosome arm, measurements of inter-homolog distance will be made at multiple positions along each arm, especially for the longer arms, by taking advantage of bar coding implemented for Oligopaints.

The methods for measuring pairing will depend to a great extent on the resolution of the chromosome paints and whether and how well they will permit the examination of decondensed chromosomes. Based in part on the methods and compositions described herein that provide Oligopaints at a very low cost, future experiments will not be limited in terms of probe and, therefore, a survey that is far-reaching and comprehensive will be able to be conducted.

Normal cells from a wide variety of tissue types will also be examined, as pairing has never been systematically assessed for humans or any mammal. Of the few studies looking for somatic pairing via FISH, probes have generally targeted only single loci on single chromosome arms and, without intending to be bound by scientific theory, it remains possible that somatic pairing is more frequent than is currently predicted. In contrast, studies will be performed with chromosome paints for all the chromosomes. Together with an analysis of transformed cells, these studies of normal cells will determine whether somatic pairing is a common feature of human cells. Whether pairing is found only in renal oncocytomas (Koeman et al. (2008) *PLoS Genetics* 4:e1000176) or in other transformed cells as well will be studied. If pairing is found outside of renal oncocytomas, it will be studied whether it is restricted to transformed cells or whether it can occur in other types of diseased tissues. Finally, if pairing can be found at a reasonable level in human cells, it will be studied whether it is restricted to only certain chromosomes. These are the important questions that can only be answered by a broad, comprehensive, and unbiased sampling of cell types.

One advantage of whole genome chromosome painting over other technologies is that it will permit the analysis of interchromosomal interactions at the single cell level. This resolution will address questions about cell-to-cell variation as well as correlations between different patterns of interchromosomal interactions that might be obscured when assays are done on large populations of cells. In short, although the methods and compositions described herein focus on pairing, Oligopaints will allow the analysis of other phenomena as well. The survey of tumor and normal cells will be an important undertaking. As pairing is a powerful modulator of gene expression, it is important, regardless of the outcome, to determine the level at which it occurs in human cells.

Experiments to identify genes in the human genome that are involved in homolog pairing will be performed by conducting a whole-genome RNAi-driven screen using FISH and chromosome paints to determine the state of pairing on Chromosome 19. The pairing extends the entire length of the q arm of Chromosome 19, from centromere to telomere. Although the q arm is maximally paired, the p arm remains entirely unpaired. Further, pairing does not extend to any of the several other chromosomes thus far examined. These three features of the pairing suggest an arm-based, rather than a locus-specific or whole-genome, mechanism for pairing. Without intending to be bound by scientific theory, one possibility for these observations is that a Chromosome 19 q-arm-specific pairing mechanism has been induced in renal oncocytomas cell lines. Alternatively, without intending to be bound by scientific theory, pairing of the q arm in renal oncocytomas may result from the release of a mechanism that normally suppresses pairing. Either way, it appears that pairing is a characteristic feature of renal oncocytomas brought about by a change that is inherited from cell-to-cell.

The gene or genes responsible for the pairing in renal oncocytomas will be identified through a whole-genome RNAi-driven screen using FISH and chromosome paints as the phenotypic assay. Following a modified version of the whole-genome, RNAi-driven, FISH-based protocol that was applied to the *Drosophila* genome, cells will be grown in 384 well plates, and they will be targeted with the repertoire of RNAi directed against approximately 20,000 human genes provided by the Institute for Chemistry and Cell Biology (ICCB) screening facility at Harvard Medical School. The impact of the RNAi will be assessed by visualizing the cells with FISH and chromosome paints targeting Chromosome 19, wherein the p and q arms will be differentially labeled. Using computer-aided analyses, RNAi species that promote pairing of the q arm not the p arm will be searched for, although any pattern of pairing among the two arms will also be of interest. All candidates will be confirmed through additional runs of RNAi, after which the genes identified by the most effective RNAi species will be characterized through standard genetic, molecular biological and biochemical studies for their role in chromosome pairing as well as tumorigenesis.

The cost of the probe for the screen described above will cost only approximately $1,200 using the Oligopaint methods and compositions described herein for Chromosome 19. This would be in sharp contrast to costs of between $90,000 (Metasystems) and $700,000 (Open Biosystems) or as much as $1,400,000 (Metasystems), if the resolution of paints to be purchased were to match that of the Oligopaints that will be synthesized for Chromosome 19.

The screen can also be carried out with Oligopaints to the entire genome so that the impact of RNAi species on the pairing of all chromosome arms can be displayed simultaneously. Oligopaint costs for such a global screen would be approximately $28,000. This global approach may be attempted or, alternatively, an approach that simultaneously targets several, but not all, of the chromosomes may be undertaken. Along these lines, a few technical modifications may be necessary in the adaptation of the *Drosophila* screening protocol to the protocol above. In particular, the *Drosophila* screen used short oligonucleotide probes containing locked nucleic acids (LNAs), which allowed a more facile adaptation of the FISH protocol to the 384-well plate format. In addition, or alternatively, Oligopaints may incorporate LNAs. If this route is taken, it may reduce the 'density' of probes in the paints in order to offset the greater cost of LNAs as compared to that of unmodified bases. In the unlikely case that neither of these approaches is successful, a screen of the human genome will be performed using a few LNA probes along Chromosome 19, following, exactly, the protocol that was used for screening the *Drosophila* genome.

REFERENCES

Koeman J M, Russell R C, Tan M H, Petillo D, Westphal M, . . . Furge K A. Somatic pairing of chromosome 19 in renal oncocytoma is associated with deregulated EGLN2-mediated [corrected] oxygen-sensing response *PLoS Genet.* 2008 July; 4(7)

Osborne C S, Chakalova L, Mitchell J A, Horton A, Wood A L, Bolland D J, Corcoran A E, Fraser P. Myc dynamically and preferentially relocates to a transcription factory occupied by Igh. *PLoS Biol.* 2007 August; 5(8):e192.

Cooper G M, Nickerson D A, Eichler E E. Mutational and selective effects on copy-number variants in the human genome. *Nat Genet.* 2007 July; 39(7 Suppl):522-9.

Matsuda K, Tanaka M, Araki S, Yanagisawa R, Yamauchi K, Koike K. Crypticinsertion into 11q23 of MLLT10 not involved in t(1; 15; 11; 10)(p36; q11; q23; q24) in infant acute biphenotypic leukemia. *Cancer Genet. Cytogenet.* 2009 Apr. 15; 190(2): 113-20

Spilianakis, C. G., M. D. Lalioti, T. Town, G. R. Lee and R. A. Flavell, 2005 Interchromosomal associations between alternatively expressed loci. *Nature* 435: 637-645.

Ling, J. Q., T. Li, J. F. Hu, T. H. Vu, H. L. Chen et al., 2006 CTCF mediates interchromosomal colocalization between Igf2/H19 and Wsb1/Nf1. *Science* 312: 269-272.

Bacher C P, Guggiari M, Brors B, Augui S, Clerc P, Avner P, Eils R, Heard E. 2006. Transient colocalization of X-inactivation centres accompanies the initiation of X inactivation. *Nat. Cell Biol.* 8:293-9. Epub 2006 Jan. 24.

Xu N, Tsai C L, Lee J T. 2006. Transient homologous chromosome pairing marks the onset of X inactivation. *Science.* 311:1149-52. Epub 2006 Jan. 19.

What is claimed is:

1. A method of making a set of high resolution oligonucleotide paints comprising:
   providing at least one solid support having a plurality of synthetic, single stranded oligonucleotide sequences attached thereto, wherein a portion of each of the plurality of synthetic, single stranded oligonucleotide sequences is complementary to a portion of a specific chromosome sequence;
   synthesizing a plurality of complementary strands, each of which is complementary to a synthetic, single stranded oligonucleotide sequence attached to the at least one solid support;
   dissociating the plurality of complementary strands from the plurality of synthetic, single stranded oligonucleotide sequences;
   amplifying the plurality of complementary strands with primers comprising an internal dU and an internal label; and
   digesting the amplified oligonucleotides with uracil-specific excision reagent to produce a set of high resolution labeled oligonucleotide paints, wherein the set of oligonucleotides paints has a resolution of about two kilobases or fewer.

2. The method of claim 1, wherein the set of oligonucleotides paints has a resolution of about one kilobase or fewer.

3. The method of claim 1, wherein the set of oligonucleotides paints has a resolution of about 100 bases or fewer.

4. The method of claim 1, wherein the set of oligonucleotides paints has a resolution of between about 20 bases and about 30 bases.

5. The method of claim 1, wherein 14 bases at each of the 3' and 5' ends of the oligonucleotide sequences are primer sequences and 32 bases internal to the primer sequences are complementary to a specific chromosome sequence.

6. The method of claim 1, wherein the label is a detectable label.

7. The method of claim 1, wherein the label is a retrievable label.

8. The method of claim 7, wherein the retrievable label further binds a moiety selected from the group consisting of a protein, a peptide, a DNA sequence, an RNA sequence and a carbohydrate.

9. The method of claim 8, wherein the retrievable moiety is exposed to light, heat or a chemical to activate binding of the retrievable label to a moiety selected from the group consisting of a protein, a peptide, a DNA sequence, an RNA sequence and a carbohydrate.

10. The method of claim 1 wherein each specific chromosome sequence excludes highly repetitive elements.

11. The method of claim 10, wherein each specific chromosome sequence excludes repetitive elements present in the genome as two copies, three copies or four copies in a haploid genome.

12. The method of claim 1, wherein the length of each of the oligonucleotide sequences is about 60 bases.

13. The method of claim 1, comprising annealing labeled primers to the single stranded oligonucleotide sequences and the label is a detectable label.

14. The method of claim 1, comprising annealing labeled primers to the single stranded oligonucleotide sequences and the label is a retrievable label.

15. The method of claim 14, wherein the retrievable label further binds a moiety selected from the group consisting of a protein, a peptide, a DNA sequence, an RNA sequence and a carbohydrate.

16. The method of claim 14, wherein the retrievable label is exposed to light, heat or a chemical to activate binding of the retrievable label to a moiety selected from the group consisting of a protein, a peptide, a DNA sequence, an RNA sequence and a carbohydrate.

17. The method of claim 13, wherein the detectable label is a fluorescent label.

18. The method of claim 13, wherein the set of oligonucleotide paints provides at least 24 spectrally resolvable labels.

19. The method of claim 13, wherein the set of oligonucleotide paints provides one spectrally resolvable color.

20. The method of claim 13, wherein the set of oligonucleotide paints provides a spectrally resolvable label for each chromosome of an organism.

21. The method of claim 13, wherein the set of oligonucleotide paints provides a spectrally resolvable label for one or more sub-chromosomal regions of an organism.

22. The method of claim 13, wherein the at least one solid support is at least one microarray.

23. The method of claim 22, wherein at least 25 microarrays are provided.

24. The method of claim 22, wherein at least 100 microarrays are provided.

25. The method of claim 1, wherein each oligonucleotide paint is complementary to a target nucleic acid sequence of 30 consecutive nucleotide bases or fewer.

26. The method of claim 1, wherein each oligonucleotide paint is complementary to a target nucleic acid sequence of 20 consecutive nucleotide bases or fewer.

27. The method of claim 1, wherein each oligonucleotide paint is complementary to a target nucleic acid sequence of 10 consecutive nucleotide bases or fewer.

28. The method of claim 1, wherein the oligonucleotide paints can cross a cell membrane.

29. The method of claim 1, wherein the oligonucleotide paints can cross a nuclear membrane.

30. The method of claim 1, further comprising the step of:
hybridizing the oligonucleotide paints to one or more target nucleic acid sequences.

31. The method of claim 1, wherein the primer includes a detectable label and a quencher.

32. The method of claim 31, wherein the quencher is released during the step of extending.

33. The method of claim 31, wherein the detectable label is a fluorescent label.

34. The method of claim 1, further comprising the step of:
hybridizing the oligonucleotide paints to one or more target sequences in the presence of an enzyme selected from the group consisting of one or more of a proteinase, a lipase, and a ribonuclease.

35. The method of claim 30, wherein the target nucleic acid sequences are present in a multi-well plate.

36. The method of claim 35, wherein the multi-well plate is a 384-well plate.

37. The method of claim 30, wherein the hybridized oligonucleotide paints are detected by fluorescent in situ hybridization (FISH).

38. The method of claim 30, wherein the one or more target nucleic acid sequences is genomic.

39. The method of claim 1 wherein the high resolution oligonucleotide paints provide strand-specific hybridization to DNA or RNA.

40. The method of claim 1, wherein each of the oligonucleotide paints has a detectable label attached to the portion that is complementary to a portion of a specific chromosome sequence.

41. The method of claim 1, wherein each of the oligonucleotide paints has a detectable label attached to an internal portion of the oligonucleotide paint.

42. The method of claim 1, wherein each of the oligonucleotide paints has an internal fluor.

43. The method of claim 1 wherein the labeled, single-stranded oligonucleotide paints include separately labeled Watson and Crick strands.

44. The method of claim 1, wherein the set of oligonucleotide paints has a resolution of an individual base pair.

45. The method of claim 1 wherein the portion of each of the plurality of synthetic, single stranded oligonucleotide sequences is complementary to a portion of a specific chromosome sequence and is flanked by primer sequences.

46. The method of claim 1 wherein the plurality of synthetic, single stranded oligonucleotide sequences are computationally patterned synthetic probes to chromosome sequences.

* * * * *